(12) United States Patent
Breu et al.

(10) Patent No.: US 6,657,060 B2
(45) Date of Patent: Dec. 2, 2003

(54) PYRIMIDINE DERIVATIVES

(75) Inventors: Volker Breu, Schliengen (DE); Frank Dautzenberg, Muellheim (DE); Patrizio Mattei, Riehen (CH); Werner Neidhart, Hagenthal le Bas (FR); Philippe Pflieger, Schwoben (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/008,166

(22) Filed: Nov. 8, 2001

(65) Prior Publication Data

US 2002/0086858 A1 Jul. 4, 2002

(30) Foreign Application Priority Data

Nov. 10, 2000 (EP) .............................. 00124610

(51) Int. Cl.[7] ................... C07D 403/04; A61K 31/506; A61P 3/04; A61P 3/10; A61P 19/02
(52) U.S. Cl. ................ 544/317; 544/322; 544/324; 544/326; 544/329; 514/256; 514/273
(58) Field of Search ............................... 544/317, 322, 544/324, 326, 329

(56) References Cited

U.S. PATENT DOCUMENTS

| 5,728,704 A | 3/1998 | Mylari et al. ............... 544/322 |
| 5,866,578 A | 2/1999 | Mylari et al. ............... 514/256 |
| 6,011,039 A | 1/2000 | Fukami et al. ............. 514/225 |

FOREIGN PATENT DOCUMENTS

| EP | 0889034 | 1/1999 |
| JP | 42004342 A | 2/1967 |
| JP | 42004345 A | 2/1967 |
| WO | WO 9407867 | 4/1994 |
| WO | WO 98 40356 A | 9/1998 |

OTHER PUBLICATIONS

XP002195673.
XP002195674.

*Primary Examiner*—Richard L. Raymond
*Assistant Examiner*—Venkataraman Balasubramanian
(74) *Attorney, Agent, or Firm*—George W. Johnston; John P. Parise

(57) ABSTRACT

Pyrimidine derivatives have been found to be useful as neuropeptide Y receptor ligands and particularly as antagonists. These pyrimidine derivatives may be used in the form of pharmaceutical preparations for the treatment or prevention of arthritis, diabetes, eating disorders, and obesity.

60 Claims, No Drawings

PYRIMIDINE DERIVATIVES

BACKGROUND OF THE INVENTION

The present invention is concerned with novel pyrimidine derivatives useful as neuropeptide Y (NPY) receptor ligands, particularly neuropeptide Y (NPY) antagonists.

SUMMARY OF THE INVENTION

The subject invention provides compounds of the formula:

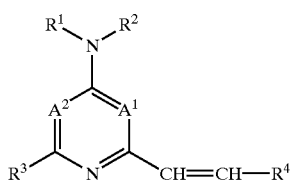

I wherein $R^1$ and $R^2$ are each independently alkyl, cycloalkyl or aralkyl, or one of $R^1$ and $R^2$ is hydrogen and the other is alkyl, aminoalkyl or cyclopropyl, or $R^1$ and $R^2$ together with the N atom to which they are attached form a 4- to 10-membered heterocylic ring or a 4- to 10-membered heterocylic ring that is substituted with one to three substituents independently selected from alkyl, hydroxy, alkoxy, alkoxyalkyl, hydroxyalkyl, and $CONR^5R^6$;

$R^3$ is alkyl, cycloalkyl, alkoxyalkyl, hydroxyalkyl, haloalkyl, alkoxy, alkoxyalkoxy, hydroxyalkoxyalkyl, hydroxyalkoxy, aralkyl or amino;

$R^4$ is aryl or heteroaryl, wherein $R^4$ is not nitro-furyl or nitro-thienyl;

$R^5$ and $R^6$ are each independently hydrogen or alkyl;

$A^1$ is CH or N; $A^2$ is CH or N; wherein one of the $A^1$ and $A^2$ is N and the other is CH;

and pharmaceutically usable salts and esters thereof.

Preferred substituents include where $R^3$ is alkyl or amino, for example methyl or methylamino. Also preferred is where $A^1$ is CH and $A^2$ is N or $A^1$ is N and $A^2$ is CH. Other favored compounds are where one of $R^1$ and $R^2$ is hydrogen and the other is alkyl, aminoalkyl or cyclopropyl, or $R^1$ and $R^2$ together with the N atom to which they are attached form a 4- to 10-membered heterocylic ring or a 4- to 10-membered heterocylic ring that is substituted with one or two substituents independently selected from alkyl, hydroxy, or alkoxy. Examples include where $R^1$ and $R^2$ together with the N atom to which they are attached form a pyrrolidine ring, a pyrrolidine ring that is substituted with alkyl, azetidine ring, or an azetidine ring that is substituted with alkyl.

$R^4$ is favorably phenyl, thienyl, furanyl, pyridinyl, or phenyl that is substituted with one to three substituents independently selected from the group consisting of halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—CH₂—O—.

Specifically provided are compounds of the formula:

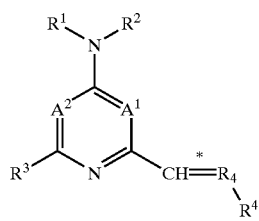

Ia wherein the double bond * is an E double bond and $R^1$ and $R^2$ are each independently alkyl, cycloalkyl or aralkyl, or one of $R^1$ and $R^2$ is hydrogen and the other is alkyl, aminoalkyl or cyclopropyl, or $R^1$ and $R^2$ together with the N atom to which they are attached form a 4- to 10-membered heterocylic ring or a 4- to 10-membered heterocylic ring that is substituted with one to three substituents independently selected from alkyl, hydroxy, alkoxy, alkoxyalkyl, hydroxyalkyl, and $CONR^5R^6$;

$R^3$ is alkyl, cycloalkyl, alkoxyalkyl, hydroxyalkyl, haloalkyl, alkoxy, alkoxyalkoxy, hydroxyalkoxyalkyl, hydroxyalkoxy, aralkyl or amino;

$R^4$ is aryl or heteroaryl, wherein $R^4$ is not nitro-furyl or nitro-thienyl;

$R^5$ and $R^6$ are each independently hydrogen or alkyl;

$A^1$ is CH or N; $A^2$ is CH or N; wherein one of the $A^1$ and $A^2$ is N and the other is CH;

and pharmaceutically usable salts and esters thereof.

The groupings mentioned above are also preferred with the compounds of formula Ia.

Some especially preferred compounds of formula Ia have $R^3$ as methyl, and $R^1$ and $R^2$ together with the N atom to which they are attached form a 4- to 10-membered heterocylic ring, such as a pyrrolidine ring. In these compounds, $R^4$ can favorably be phenyl that is substituted with one to three substituents independently selected from the group consisting of halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—CH₂—O—.

Other favored compounds of formula Ia have $R^4$ as thienyl or pyridinyl. Alternatively, $R^1$ and $R^2$ together with the N atom to which they are attached form a piperidine ring and $R^4$ can be phenyl that is substituted with one to three substituents independently selected from the group consisting of halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—CH₂—O—. $R^1$ and $R^2$ together with the N atom to which they are attached can also favorably form an azetidine ring that is substituted with alkyl, such as methyl. $R^3$ can also favorably be methylamino.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The invention is concerned with compounds of formula I

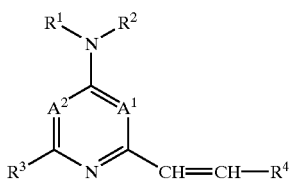

wherein

R¹ and R² are each independently alkyl, cycloalkyl or aralkyl or one of R¹ and R² is hydrogen and the other is alkyl, aminoalkyl or cyclopropyl or R¹ and R² together with the N atom to which they are attached form a 4- to 10-membered heterocylic ring optionally substituted with one to three substituents independently selected from alkyl, hydroxy, alkoxy, alkoxyalkyl, hydroxyalkyl or CONR⁵R⁶;

R³ is alkyl, cycloalkyl, alkoxyalkyl, hydroxyalkyl, haloalkyl, alkoxy, alkoxyalkoxy, hydroxyalkoxyalkyl, hydroxyalkoxy, aralkyl or amino;

R⁴ is aryl or heteroaryl, wherein R⁴ is not nitro-furyl or nitro-thienyl;

R⁵ and R⁶ are each independently hydrogen or alkyl;

A¹ is CH or N; A² is CH or N; wherein one of the A¹ and A² is N and the other is CH;

and pharmaceutically usable salts and esters thereof

The compounds of formula I and their pharmaceutically usable salts and esters are novel and have valuable pharmacological properties. They are neuropeptide ligands, for example neuropeptide receptor antagonists and in particular, they are selective neuropeptides Y Y5 receptor antagonists.

Neuropetide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonize neuropetide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on associated risk factors such as arthritis and diabetes.

Accordingly, the compounds of formula I maybe used in the prophylaxis or treatment of arthritis, diabetes and particularly eating disorders and obesity.

The subject invention provides the compounds of formula I and their aforementioned salts and esters per se and their use as therapeutically active substances, a process for the manufacture of the said compounds, intermediates, pharmaceutical compositions, medicaments containing the compounds, their pharmaceutically usable salts and esters, the use of the said compounds salts and esters for the prophylaxis and/or therapy of illnesses, especially in the treatment or prophylaxis of arthritis, diabetes and particularly eating disorders such as hyperphagia and particularly obesity, and the use of the compounds, salts and esters for the production of medicaments for the treatment or prophylaxis of arthritis, diabetes and particularly eating disorders and obesity.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "haloalkyl", alone or in combination, signifies an alkyl or cycloalkyl group, preferably an alkyl group, as previously defined in which one to three hydrogen atoms have been replaced by halogen atoms. Preferred examples are trichloromethyl or trifluoromethyl. Particularly preferred is trifluoromethyl.

The term "alkylsulfanyl" alone or in combination means an alkyl-S— group in which alkyl is as previously defined.

The term "alkylsulfonyl" alone or in combination means an

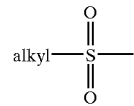

group in which alkyl is as previously defined.

The term "aminosulfonyl" alone or in combination means an

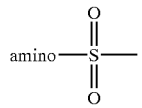

group in which amino is as previously defined.

The term "hydroxyalkyl", alone or in combination, signifies a alkyl group as previously described, wherein one or two, preferably one, hydrogen atom has been replaced by a hydroxy group. A preferred example is hydroxymethyl.

The term "alkoxy", alone or in combination, signifies a group of the formula alkyl—O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxypreferably methoxy and ethoxy and most preferred methoxy.

The term "alkoxyalkyl", alone or in combination, signifies a alkyl group as previously described, wherein one or two, preferably one, hydrogen atom has been replaced by an alkoxy group. Preferred examples are methoxymethyl and ethoxymethyl.

The term "hydroxyalkoxyalkyl", alone or in combination, signifies an alkyl group as previously described, wherein one or two, preferably one, hydrogen atom has been replaced by a hydroxyalkoxy group. A preferred example is hydroxyethoxymethyl.

The term "alkoxyalkoxy", alone or in combination, signifies a group of the formula alkyl-O-alkyl-O— in which the term "alkyl" has the previously given significance. A preferred example is 2-methoxyethoxy.

The term "hydroxyalkoxy", alone or in combination, signifies alkoxy group as previously described in which one hydrogen atom has been replaced by a hydroxy group. Examples are 3-hydroxypropoxy and preferably 2-hydroxyethoxy.

The term "aryl", alone or in combination, signifies a phenyl or naphthyl group, preferably a phenyl group, which optionally carry one to four, preferably one to three, particularly preferred one or two substituents independently selected from halogen, halogenoalkyl, nitro, alkoxy, cyano, amino, —O—$(CH_2)_{1-3}$—O—, hydroxy, heterocyclyl, alkylsulfanyl, alkylsulfonyl, aralkoxy, alkoxycarbonyl, hydroxyalkyl, aminosulfonyl and alkylsulfonylamino. Preferred substituents of aryl are halogen, halogenoalkyl, nitro, alkoxy, cyano, amino, —O—$(CH_2)_1$—O—, hydroxy, tetrazolyl, alkylsulfanyl, alkylsulfonyl, aralkoxy, alkoxycarbonyl, hydroxyalkyl and aminosulfonyl. Particularly preferred substituents of aryl are trifluoromethyl, nitro, cloro, fluoro, alkoxy, cyano, dimethylamino, —O—$(CH_2)$—O—, hydroxy, 2H-tetrazol-5-yl, alkylsulfanyl, alkylsulfonyl, benzyloxy, alkoxycarbonyl, hydroxymethyl, diaminosulfonyl and primary amino. Examples of such aryl groups are are trifluoromethylphenyl, nitrophenyl, clorophenyl, methoxyphenyl, dimethoxyphenyl, cyanophenyl, dichlorophenyl, dimethylaminophenyl, 2-benzo(1,3)dioxol-5-yl, hydroxyphenyl, (2H-tetrazol-5-yl)-phenyl, methylsulfanyl, methylsulfonyl, fluorophenyl, benzyloxy-phenyl, methoxycarbonyl-phenyl, difluorophenyl, hydroxymethylen-phenyl, chlorofluorophenyl, dimethylaminosulfonylphenyl and aminophenyl.

The term "aralkyl", alone or in combination, signifies an alkyl or cycloalkyl group as previously defined in which one hydrogen atom has been replaced by a phenyl or naphthyl group which optionally carries one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro and the like. Examples of aralkyl groups are benzyl, benzyl substituted with hydroxy, alkoxy or halogen, preferably fluorine. Particularly preferred is benzyl.

The term "heterocyclyl", as used in the definition of the term aryl, alone or in combination signifies a mono- or bicyclic carbocyclic ring having 5 to 10, preferably 5 to 6 ring atoms, comprising one to five heteroatoms, preferably one to four heteroatoms, independently selected from nitrogen, oxygen or sulfur, preferrably nitrogen. Optionally, the heterocyclyl group is mono, di- or trisubstituted, independently with alkyl or halogen. Examples of such heterocyclyl groups are pyrrolyl, tetrazolyl, oxazolyl, imidazolyl, thiazolyl and pyrimidinyl. A preferred example is 2H-tetrazol-5-yl.

The term "heteroaryl" alone or in combination sigifies an aromatic mono- or bicyclic carbocyclic ring having 5 to 10, preferably 5 to 6 ring atoms, containing one to three heteroatoms, preferably one heteroatom, e.g. independently selected from nitrogen, oxygen or sulfur. Examples of heteroaryl groups are pyrimidinyl, pyridinyl, thiophenyl, oxazolyl, thiazolyl and furanyl. Optionally, the heteroaryl group can be mono-, di- or tri-substituted, independently, with methyl or halogen. Preferred examples are thienyl, pyridinyl, furanyl and 2,6-dimetyl-pyrimidin-4-yl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methylethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine and particularly fluorine or chlorine.

The term "pharmaceutically usable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically usable salt also includes physiologically usable solvates.

"Pharmaceutically usable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application W099/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

A preferred aspect of the present invention are compounds according to formula I, wherein $R^3$ is alkyl or amino and particularly preferred methyl or methylamino. Most preferred is methyl.

Another preferred aspect of the invention are compounds of formula I, wherein $A^1$ is CH and $A^2$ is N. Particularly preferred are compounds of formula I, wherein $A^1$ is N and $A^2$ is CH.

Also preferred compounds of formula I are those, wherein one of $R^1$ and $R^2$ is hydrogen and the other is alkyl, aminoalkyl or cyclopropyl or $R^1$ and $R^2$ together with the N atom to which they are attached form a 4- to 10-membered heterocylic ring optionally substituted with one or two substituents independently selected from alkyl, hydroxy, or alkoxy. Preferred 4- to 10-membered heterocyclic rings are carbocyclic rings optionally comprising one or two, preferably one, further heteroatom independently selected from O, N and S, wherein N and particularly O are preferred, in addition to the N atom to which $R^1$ and $R^2$ are attached. Examples of these heterocyclic rings are azetidine, pyrrolidine, piperidine, hexamethyleneimine, morpholine, thiomorpholine, piperazine and terahydroisoquinoline. Preferred 4- to 10-membered heterocyclic rings which are formed by $R^1$ and $R^2$ together with the N atom to which they are attached are pyrrolidine, piperidine, morpholine, tetrahydro-isoquinoline and azetidine. Particularly preferred compounds of formula I are those, wherein $R^1$ and $R^2$ together with the N atom to which they are attached form a pyrrolidine or an azetidine optionally substituted with alkyl. Most preferred are pyrrolidine and methyl-azetidine.

Particularly preferred compounds of formula I are those, wherein $R^4$ is phenyl optionally substituted with one to three substituents independently selected from halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—CH$_2$—O— or $R^4$ is thienyl, furanyl or pyridinyl.

Another aspect of the invention are compounds of formula Ib

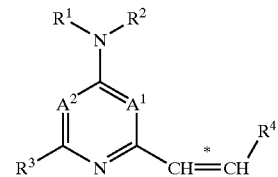

Ib wherein the double bond * is a Z double bond and $A^1$, $A^2$ and $R^1$ to $R^4$ are defined as before. Z double bond means that $R^4$ and the pyrimidine ring are on the same side of the double bond. Particularly preferred are compounds of formula Ia

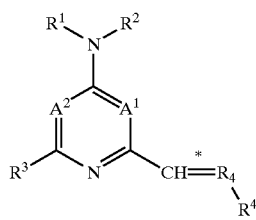

Ia wherein the double bond * is an E double bond and $A^1$, $A^2$ and $R^1$ to $R^4$ are defined as before. E double bond means that $R^4$ and the pyrimidine ring are not on the same side of the double bond.

Examples of preferred compounds of formula I are:
(E)-2-methyl-4-pyrrolidin-1-yl-6-[2-(3-trifluoromethyl-phenyl)-vinyl]-pyrimidine;
(E)-4-methyl-6-pyrrolidin-1-yl-2-[2-(3-trifluoromethyl-phenyl)-vinyl]-pyrimidine;
(E)-2-methyl-4-piperidin-1-yl-6-[2-(3-trifluoromethyl-phenyl)-vinyl]-pyrimidine;
(E)-4-methyl-6-piperidin-1-yl-2-[2-(3-trifluoromethyl-phenyl)-vinyl]-pyrimidine;
(E)-4-{2-methyl-6-[2-(3-trifluoromethyl-phenyl)-vinyl]-pyrimidin-4-yl}-morpholine;
(E)-4-{6-methyl-2-[2-(3-trifluoromethyl-phenyl)-vinyl]-pyrimidin-4-yl}-morpholine;
(E)-2-{2-methyl-6-[2-(3-trifluoromethyl-phenyl)-vinyl]-pyrimidin-4-yl}-1,2,3,4-tetrahydroisoquinoline;
(E)-2-{6-methyl-2-[2-(3-trifluoromethyl-phenyl)-vinyl]-pyrimidin-4-yl}-1,2,3,4-tetrahydroisoquinoline;
(E)-2-methyl-4-[2-(3-nitro-phenyl)-vinyl]-6-pyrrolidin-1-yl-pyrimidine;
(E)-2-methyl-4-[2-(3-nitro-phenyl)-vinyl]-6-piperidin-1-yl-pyrimidine;
(E)-4-methyl-2-[2-(3-nitro-phenyl)-vinyl]-6-piperidin-1-yl-pyrimidine;
(E)-2-[2-(3-chloro-phenyl)-vinyl]-4-methyl-6-pyrrolidin-1-yl-pyrimidine;
(E)-4-methyl-6-pyrrolidin-1-yl-2-(2-thiophen-2-yl-vinyl)-pyrimidine;
(E)-2-[2-(4-methoxy-phenyl)-vinyl]-4-methyl-6-pyrrolidin-1-yl-pyrimidine;
(E)-2-[2-(2,4-dimethoxy-phenyl)-vinyl]-4-methyl-6-pyrrolidin-1-yl-pyrimidine;
(E)-4-[2-(4-methyl-6-pyrrolidin-1-yl-pyrimidin-2-yl)-vinyl]-benzonitrile;
(E)-2-[2-(3,4-dichloro-phenyl)-vinyl]-4-methyl-6-pyrrolidin-1-yl-pyrimidine;
(E)-2-[2-(2,4-dichloro-phenyl)-vinyl]-4-methyl-6-pyrrolidin-1-yl-pyrimidine;
(E)-cyclopropyl-{2-[2-(2,4-dichloro-phenyl)-vinyl]-6-methyl-pyrimidin-4-yl}-amine;
(E)-3-[2-(4-methyl-6-pyrrolidin-1-yl-pyrimidin-2-yl)-vinyl]-benzonitrile;
(E)-3-[2-(4-cyclopropylamino-6-methyl-pyrimidin-2-yl)-vinyl]-benzonitrile;
(E)-{2-[2-(3-chloro-phenyl)-vinyl]-6-methyl-pyrimidin-4-yl}-cyclopropyl-amine;
(E)-3-{2-[4-(3-methyl-azetidin-1-yl)-6-methyl-pyrimidin-2-yl]-vinyl}-benzonitrile;
(E)-2-[2-(3-chloro-phenyl)-vinyl]-4-methyl-6-(3-methyl-azetidin-1-yl)-pyrimidine;
(E)-3-{2-[4-(3-hydroxy-pyrrolidin-1-yl)-6-methyl-pyrimidin-2-yl]-vinyl}-benzonitrile;
(E)-3-[2-(4-butylamino-6-methyl-pyrimidin-2-yl)-vinyl]-benzonitrile;
(E)-3-dimethyl-{4-[2-(4-methyl-6-pyrrolidin-1-yl-pyrimidin-2-yl)-vinyl]-phenyl}-amine;
(E)-2-(2-benzo[1,3]dioxol-5-yl-vinyl)-4-methyl-6-pyrrolidin-1-yl-pyrimidine;
(E)-2-[2-(3-methoxy-phenyl)-vinyl]-4-methyl-6-pyrrolidin-1-yl-pyrimidine;
(E)4-(3-ethoxy-pyrrolidin-1-yl)-2-[2-(3-methoxy-phenyl)-vinyl]-6-methyl-pyrimidine;
(E)-2-[2-(3-hydroxy-phenyl)-vinyl]-4-methyl-6-pyrrolidin-1-yl-pyrimidine;
(E)-3-{2-[4-(2-amino-ethylamino)-6-methyl-pyrimidin-2-yl]-vinyl}-benzonitrile;
(E)-3-{2-[4-(3-ethoxy-pyrrolidin-1-yl)-6-methyl-pyrimidin-2-yl]-vinyl}-benzonitrile;
(E)-4-methyl-6-pyrrolidin-1-yl-2-{2-[3-(2H-tetrazol-5-yl)-phenyl]-vinyl}-pyrimidine;
(E)-4-methyl-2-[2-(4-methylsulfanyl-phenyl)-vinyl]-6-pyrrolidin-1-yl-pyrimidine;
2-[2-(4-methanesulfonyl-phenyl)-vinyl]-4-methyl-6-pyrrolidin-1-yl-pyrimidine;
(E)-2-[2-(3-fluoro-phenyl)-vinyl]-4-methyl-6-pyrrolidin-1-yl-pyrimidine;
(E)-4-(3-ethoxy-pyrrolidin-1-yl)-2-[2-(3-fluoro-phenyl)-vinyl]-6-methyl-pyrimidine;
(E)-2-[2-(3-benzyloxy-phenyl)-vinyl]-4-methyl-6-pyrrolidin-1-yl-pyrimidine;
(E)-3-[2-(4-methyl-6-pyrrolidin-1-yl-pyrimidin-2-yl)-vinyl]-benzoic acid methyl ester;
(E)-{3-[2-(4-methyl-6-pyrrolidin-1-yl-pyrimidin-2-yl)-vinyl]-phenyl}-methanol;
(E)-2-[2-(3,4-difluoro-phenyl)-vinyl]-4-methyl-6-pyrrolidin-1-yl-pyrimidine;
(E)-2-[2-(2,4-difluoro-phenyl)-vinyl]-4-methyl-6-pyrrolidin-1-yl-pyrimidine;
(E)-2-[2-(4-fluoro-3-chloro-phenyl)-vinyl]-4-methyl-6-pyrrolidin-1-yl-pyrimidine;
(E-)4-methoxy-N,N-dimethyl-3-[2-(4-methyl-6-pyrrolidin-1-yl-pyrimidin-2-yl)-vinyl]-benzenesulfonamide;
(E)-4-methyl-2-[2-(3-nitro-phenyl)-vinyl]-6-pyrrolidin-1-yl-pyrimidine;
(E)-3-[2-(4-methyl-6-pyrrolidin-1-yl-pyrimidin-2-yl)-vinyl]-phenylamine;
(E)-2-[2-(3,5-dichloro-phenyl)-vinyl]-4-methyl-6-pyrrolidin-1-yl-pyrimidine;
(E)-4-methyl-2-(2-pyridin-2-yl-vinyl)-6-pyrrolidin-1-yl-pyrimidine;
(E)-4-methyl-2-(2-pyridin-4-yl-vinyl)-6-pyrrolidin-1-yl-pyrimidine;
(E)-methyl-[2-(2-pyridin-2-yl-vinyl)-6-pyrrolidin-1-yl-pyrimidin-4-yl]-amine;
(E)-methyl-[2-(2-pyridin-4-yl-vinyl)-6-pyrrolidin-1-yl-pyrimidin-4-yl]-amine.

Examples of particularly preferred compounds of formula I are:
(E)-4-methyl-6-pyrrolidin-1-yl-2-[2-(3-trifluoromethyl-phenyl)-vinyl]-pyrimidine;
(E)-2-[2-(3-chloro-phenyl)-vinyl]-4-methyl-6-pyrrolidin-1-yl-pyrimidine;
(E)-2-[2-(2,4-dichloro-phenyl)-vinyl]-4-methyl-6-pyrrolidin-1-yl-pyrimidine;
(E)-3-[2-(4-methyl-6-pyrrolidin-1-yl-pyrimidin-2-yl)-vinyl]-benzonitrile;
(E)-3-{2-[4-(3-methyl-azetidin-1-yl)-6-methyl-pyrimidin-2-yl]-vinyl}-benzonitrile;
(E)-2-[2-(3-methoxy-phenyl)-vinyl]-4-methyl-6-pyrrolidin-1-yl-pyrimidine;
(E)-{3-[2-(4-methyl-6-pyrrolidin-1-yl-pyrimidin-2-yl)-vinyl]-phenyl}-methanol;

(E)-2-[2-(3,4-difluoro-phenyl)-vinyl]-4-methyl-6-pyrrolidin-1-yl-pyrimidine;
(E)-2-[2-(4-fluoro-3-chloro-phenyl)-vinyl]-4-methyl-6-pyrrolidin-1-yl-pyrimidine;
(E)-methyl-[2-(2-pyridin-4-yl-vinyl)-6-pyrrolidin-1-yl-pyrimidin-4-yl]-amine.

Processes for the manufacture of compounds of formula I are an object of the invention.

The substituents and indices used in the following description of the processes have the significance given above unless indicated to the contrary.

Compounds of Formula I can be Obtained by the Following Methods

According to scheme 1, compounds of formula II, with Hal meaning chloro or bromo, can be reacted with the corresponding amines in a suited solvent such as methanol, isopropanol or THF—or without solvent—to yield the amino derivatives of general formula III selectively. The compounds of type III can then be reacted in a Pd-catalysed coupling reaction (Heck-type reaction; for a review: M. Beller et al: 'Palladium-catalysed olefination of aryl halides and related transformations', Transition Metals for Organic Synthesis, Vol 1, 1998, Wiley-VCH), with appropriate olefins XI as defined above, in the presence of phosphines, such as tris-(o-tolyl)phosphine or tri-t-butylphosphine in DMF and with $NaHCO_3$ or $CsCO_3$ as a base, to give compounds of general formula I. In case mixtures of isomers are obtained these isomers can be separated by chromatography. Alternatively, compound III can be reacted with a corresponding acetylen derivative of formula $CH\equiv C-R^4$ (XIV) in a Sanagashira-type coupling with $Pd(PPh_3)_4$, CuI in trietylamine as base and solvent (for general procedure: K. Sonogashira in Synthesis, 1977 p 777) followed by reduction either via hydrogenation with Lindlar catalyst in ethanol or benzene as solvent (for an analogous procedure: X. Huang, Synthesis 1995, p 769) or with sodium bis(2-methoxy)aluminium hydride (Red-Al) in a suited solvent such as THF (for a general procedure: M. F. Semmelhack, J. Org. Chem., 1975 p 3619).

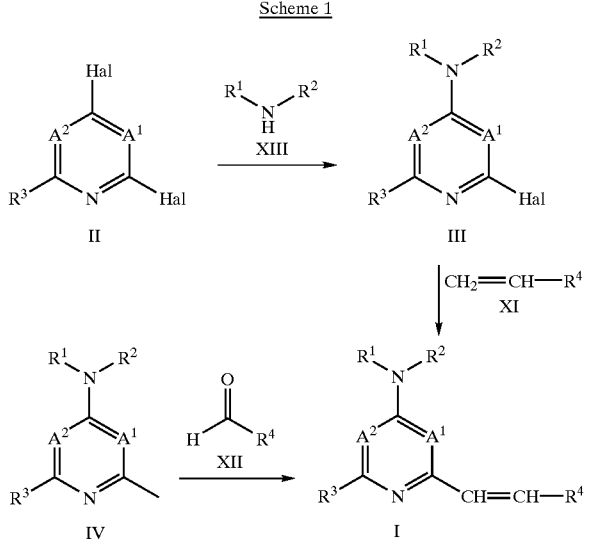

Scheme 1

(b) Alternatively, according to scheme 1, compounds of formula I can be obtained from compounds of type IV on reaction with appropriate aldehydes XII in acetic anhydride or propionic anhydride as a solvent, at elevated temperatures, in analogy to a procedure described by A. Fujita (Chem. Pharm. Bull, 1965, p 1183).

(c) A further alternative summarized in scheme 2 consists of reacting a methyl hydroxypyrimidine of formula V with an appropriate aldehyde in an aldol-type condensation as above to yield compounds of formula VI. In cases were $R^3$ is Me, either one of the Me groups reacts selectively with the aldehyde (depending on $A^2$ and $A^1$ definitions) or the mixtures obtained are seperated by chromatography to give the compounds of formula VI. The transformations to compounds of formula I can be achieved following a standard reaction sequence comprising halogenation with e.g. $POCl_3$ (or $POBr_3$) to give compounds of type VII and subsequent substitution with appropriate amines as described above.

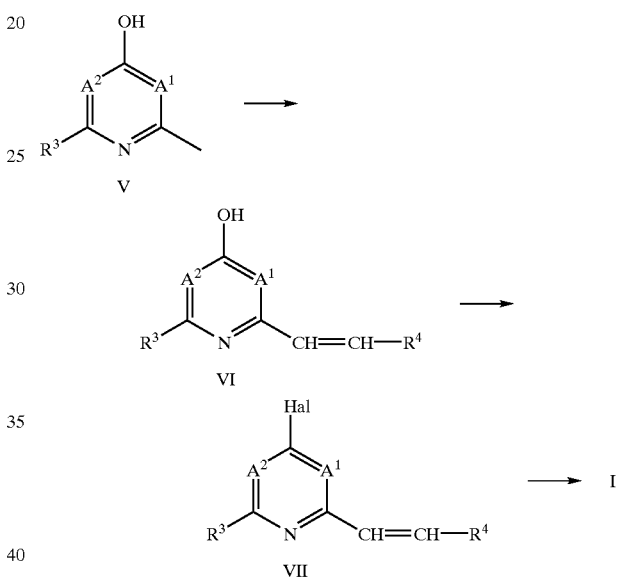

Scheme 2

(d) A further alternative to prepare compounds of type I consists of reacting pyrimidinyl aldehydes of general type VIII with suited Wittig salts as outlined in scheme 3 or to condensate appropriately substituted Wittig salts of type IX with the corresponding aldehydes.

The compounds of formula IX can be obtained from VIII by standard transformation known in the art (reduction of the aldehyde, halogenation followed by Wittig salt formation). Depending on the reaction conditions mixtures of (E) and (Z) isomers can be obtained, which can be separated by chromatographic methods (e.g. preparative HPLC), or the thermodynamically more stable (E)-isomers Ia or the kinetically favoured (Z)-isomers Ib can be obtained as main products, receptively. Thus, for example, under 'salt free' and 'high dilution' conditions in THF as solvent the (Z) isomer can be obtained selectively, whereas in the presence of lithium salts and under 'high concentration' conditions the (E) isomer can be obtained(for a general review: W. Carruthers: Some Modern Methods of Organic Synthesis, 2th Ed., Cambridge Texts in Chemistry and Biochemistry, 1978 and: B. E. Maryanoff; J. Org. Chem. 1986, p 3302).

Scheme 3

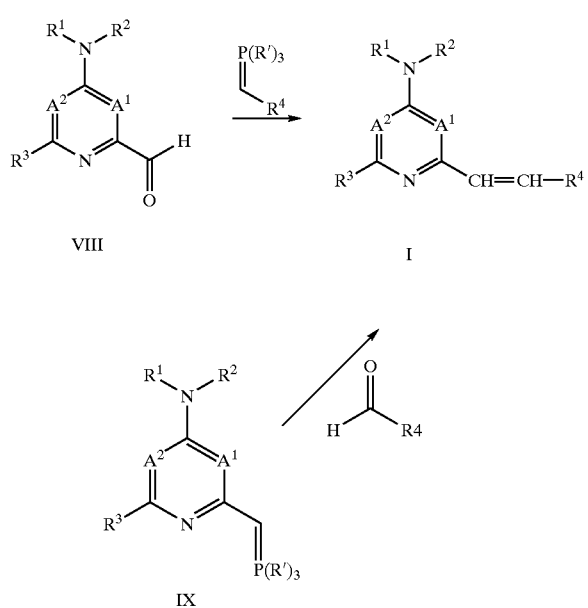

R' means e.g. phenyl

Preparation of the Intermediates

The starting materials of general formula III are either known in the literature or can be obtained on application of classic methods of of pyrimidine synthesis and subsequent functional group conversion from amidines (or urea) and malonic acid derivatives as illustrated in scheme 4—taking into account the definitions $A^2$ and $A^1$, and $R^3$. Halogenation of the pyrimidine-diol intermediates X to provide compounds of general formula II can be accomplished with e.g. $POCl_3$ or $POBr_3$, as described above.

Scheme 4

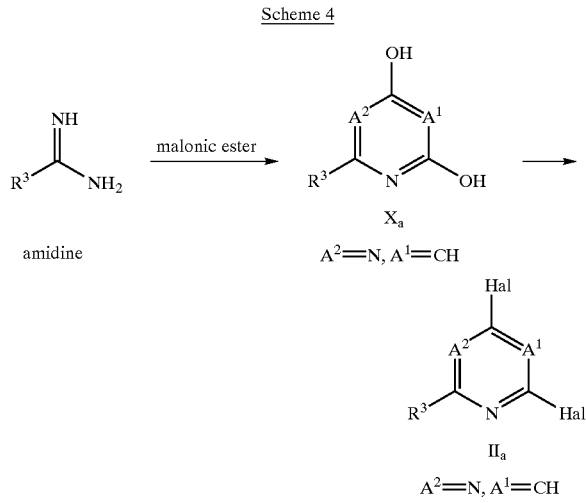

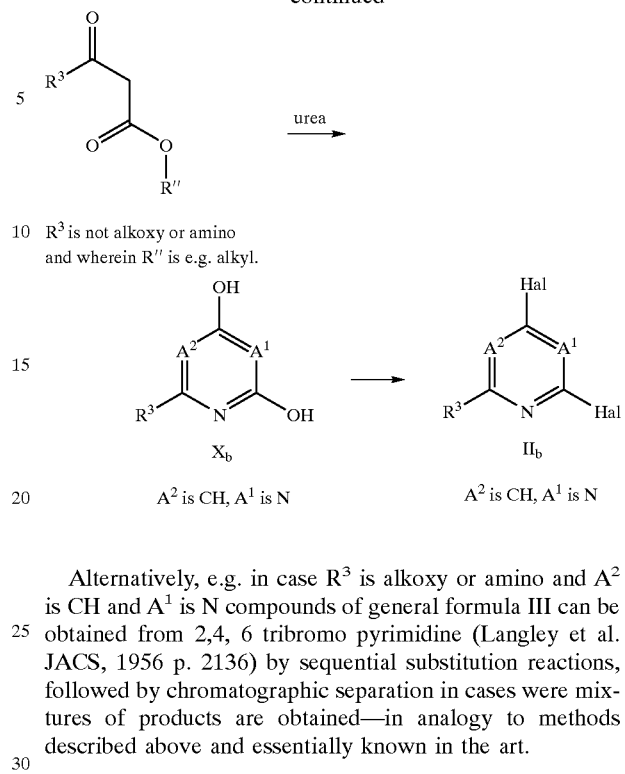

$R^3$ is not alkoxy or amino and wherein R″ is e.g. alkyl.

Alternatively, e.g. in case $R^3$ is alkoxy or amino and $A^2$ is CH and $A^1$ is N compounds of general formula III can be obtained from 2,4, 6 tribromo pyrimidine (Langley et al. JACS, 1956 p. 2136) by sequential substitution reactions, followed by chromatographic separation in cases were mixtures of products are obtained—in analogy to methods described above and essentially known in the art.

Scheme 5

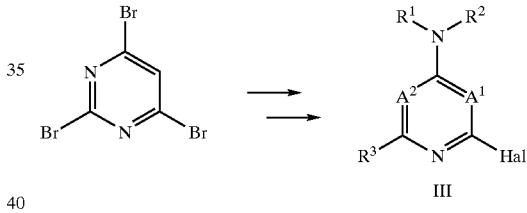

Compound of formula IV are essentially known in the literature (e.g. J. Org. Chem. 1987, p.1017), from which the pyrimidinyl aldehydes of formula VIII can be be obtained by oxydation, following general procedures as described in the literature: e.g. H. Yamanaka, Chem. Pharm. Bull, 1984, p 2005. Compounds of formula V are either commercially available, described in the literature or easily obtained by standard procedures of pyrimidine synthesis, in analogy to sequences illustrated in scheme 4. Thus, from condensation of an amidine according to scheme 4 with alkyl acetoacetate there can be obtained compounds of general formula V with $A^2$ is N, $A^1$ is CH. Compounds of formula V with ($A^2$ is CH, $A^1$ is N, $R^3$ is not alkoxy or amino) can be prepared as for $X_b$ scheme 4, replacing urea with acetamidine and, in the cases were $R^3$ is alkoxy or amino, from methyl amidine and malonic ester (or alkyl cyanoacetate for $R^3$ is amino) in analogy to Xa, scheme 4, followed by functional group transformations known in the literature.

In case a mixture of compounds according to formula Ia and Ib is obtained according to any one of the mentioned reactions separation is possible by methods known in the art such as chromatography.

A preferred process for the preparation of a compound of formula I comprises one of the following reactions a)

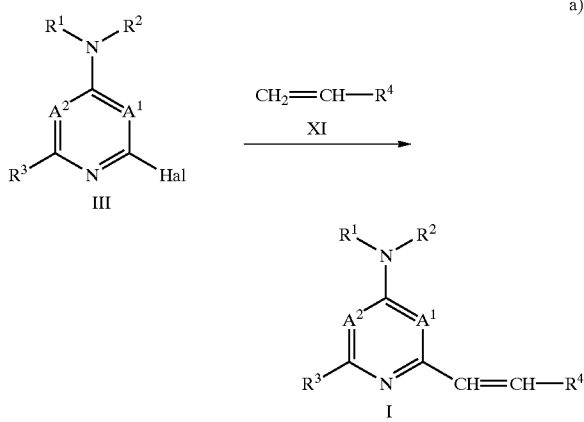

the reaction of a compound according to formula III in the presence of a compound of formula XI, wherein $R^1$, $R^2$, $R^3$, $R^4$, $A^1$ and $A^2$ are $R^1$ and $R^2$ are each independently alkyl, cycloalkyl or aralkyl, or one of $R^1$ and $R^2$ is hydrogen and the other is alkyl, aminoalkyl or cyclopropyl, or $R^1$ and $R^2$ together with the N atom to which they are attached form a 4- to 10-membered heterocylic ring or a 4- to 10-membered heterocylic ring that is substituted with one to three substituents independently selected from alkyl, hydroxy, alkoxy, alkoxyalkyl, hydroxyalkyl, and $CONR^5R^6$; $R^3$ is alkyl, cycloalkyl, alkoxyalkyl, hydroxyalkyl, haloalkyl, alkoxy, alkoxyalkoxy, hydroxyalkoxyalkyl, hydroxyalkoxy, aralkyl or amino; $R^4$ is aryl or heteroaryl, wherein $R^4$ is not nitro-furyl or nitro-thienyl; $R^5$ and $R^6$ are each independently hydrogen or alkyl; $A^1$ is CH or N; $A^2$ is CH or N; wherein one of the $A^1$ and $A^2$ is N and the other is CH. Hal means chloro or bromo. In a preferred aspect the above reaction is performed in the presence of a transition metal catalyst, particularly palladium and particularly in the presence of a phosphine.

b)

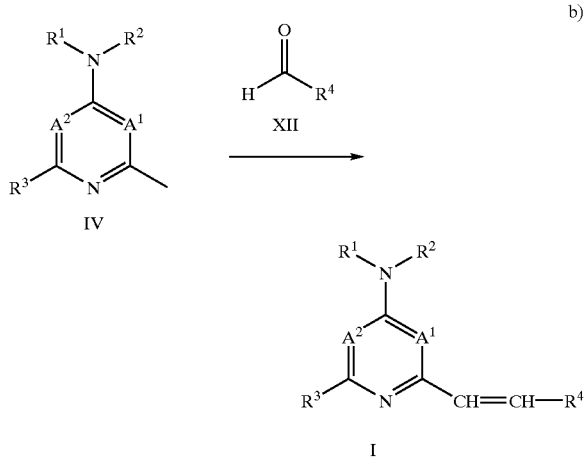

the reaction of a compound according to formula IV in the presence of a compound of formula XII, wherein $R^1$, $R^2$, $R^3$, $R^4$, $A^1$ and $A^2$ are defined as above;

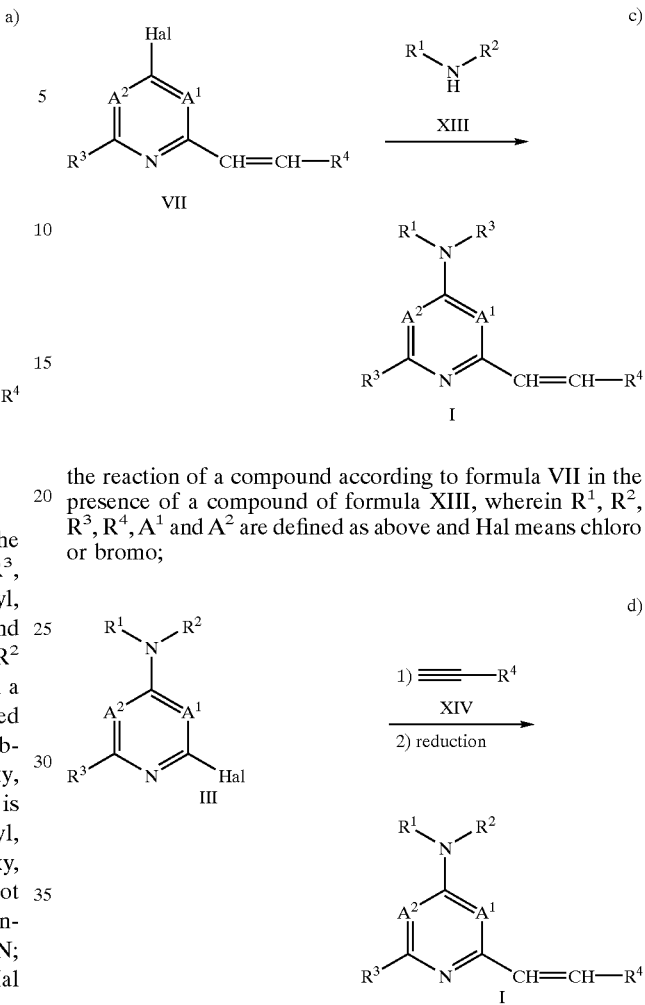

the reaction of a compound according to formula VII in the presence of a compound of formula XIII, wherein $R^1$, $R^2$, $R^3$, $R^4$, $A^1$ and $A^2$ are defined as above and Hal means chloro or bromo;

the reaction of a compound according to formula III in the presence of a compound of formula XIV and subsequently reduction, wherein $R^1$, $R^2$, $R^3$, $R^4$, $A^1$ and $A^2$ are defined as above and Hal means chloro or bromo.

The invention also includes intermediates of formula III VI and VII.

Preferred intermediates of formula III are:
2-chloro-4-methyl-6-pyrrolidin-1-yl-pyrimidine;
2-bomo-6-pyrrolidin-1-yl-pyrimidin-4-yl)-methyl-amine.

Preferred intermediates of formula VI and VII are:
(E) 4-chloro-2-[2-(3-chloro-phenyl)-vinyl]-6-methyl-pyrimidine;
(E)-4-chloro-6-methyl-2-(2-thiophen-2-yl-vinyl)-pyrimidine;
(E)-4-chloro-2-[2-(4-methoxy-phenyl)-vinyl]-6-methyl-pyrimidine;
(E)-4-chloro-2-[2-(2,4-dimethoxy-phenyl)-vinyl]-6-methyl-pyrimidine;
(E)-4-[2-(4-chloro-6-methyl-pyrimidin-2-yl)-vinyl]-benzonitrile;
(E)-4-chloro-2-[2-(3,4-dichloro-phenyl)-vinyl]-6-methyl-pyrimidine;
4-chloro-2-[2-(2,4-dichloro-phenyl)-vinyl]-6-methyl-pyrimidine;
(E)-4-chloro-2-[2-(2,4-dichloro-phenyl)-vinyl]-6-methyl-pyrimidine;
(E)-3-[2-(4-chloro-6-methyl-pyrimidin-2-yl)-vinyl]-benzonitrile;

(E)-3-[2-(4-chloro-6-methyl-pyrimidin-2-yl)-vinyl]-benzonitrile;
(E)-4-chloro-2-[2-(3-chloro-phenyl)-vinyl]-6-methyl-pyrimidine;
(E)-3-[2-(4-chloro-6-methyl-pyrimidin-2-yl)-vinyl]-benzonitrile;
(E)-4-chloro-2-[2-(3-chloro-phenyl)-vinyl]-6-methyl-pyrimidine;
(E)-3-[2-(4-chloro-6-methyl-pyrimidin-2-yl)-vinyl]-benzonitrile;
(E)-3-[2-(4-chloro-6-methyl-pyrimidin-2-yl)-vinyl]-benzonitrile;
(E)-4-chloro-2-[2-(4-dimethylamino-phenyl)-vinyl]-6-methyl-pyrimidine;
(E)-2-(2-benzo [1,3]dioxol-5-yl-vinyl)-4-chloro-6-methyl-pyrimidine;
(E)-4-chloro-2-[2-(3-methoxy-phenyl)-vinyl]-6-methyl-pyrimidine;
(E)-4-chloro-2-[2-(3-methoxy-phenyl)-vinyl]-6-methyl-pyrimidine;
(E)-2-[2-(3-methoxy-phenyl)-vinyl]-4-methyl-6-pyrrolidin-1-yl-pyrimidine;
(E)-3-[2-(4-chloro-6-methyl-pyrimidin-2-yl)-vinyl]-benzonitrile;
(E)-3-[2-(4-chloro-6-methyl-pyrimidin-2-yl)-vinyl]-benzonitrile;
(E)-3-[2-(4-methyl-6-pyrrolidin-1-yl-pyrimidin-2-yl)-vinyl]-benzonitrile;
(E)-4-chloro-6-methyl-2-[2-(4-methylsulfanyl-phenyl)-vinyl]-pyrimidine;
(E)-4-chloro-6-methyl-2-[2-(4-methyl-sulfanyl-phenyl)-vinyl]-pyrimidine;
(E)-4-chloro-6-methyl-2-[2-(3-fluoro-phenyl)-vinyl]-pyrimidine;
(E)-4-chloro-6-methyl-2-[2-(3-fluoro-phenyl)-vinyl]-pyrimidine;
(E)-2-[2-(3-benzyloxy-phenyl)-vinyl]-4-chloro-6-methyl-pyrimidine;
(E)-3-[2-(4-chloro-6-methyl-pyrimidin-2-yl)-vinyl]-benzoic acid methyl ester;
(E)-3-[2-(4-methyl-6-pyrrolidin-1-yl-pyrimidin-2-yl)-vinyl]-benzoic acid methyl ester;
(E)-4-chloro-2-[2-(3,4-difluoro-phenyl)-vinyl]-6-methyl-pyrimidine;
(E)-4-chloro-2-[2-(2,4-difluoro-phenyl)-vinyl]-6-methyl-pyrimidine;
(E)-4-chloro-2-[2-(3-chloro-4-fluoro-phenyl)-vinyl]-6-methyl-pyrimidine;
(E)-3-[2-(4-chloro-6-methyl-pyrimidin-2-yl)-vinyl]-4-methoxy-N,N-dimethylbenzenesulfonamide;
(E)-4-chloro-2-[2-(3-nitro-phenyl)-vinyl]-6-methyl-pyrimidine;
(E)-4-methyl-2-[2-(3-nitro-phenyl)-vinyl]-6-pyrrolidin-1-yl-pyrimidine;
4-chloro-2-[2-(3,5-dichloro-phenyl)-vinyl]-6-methyl-pyrimidine.

The compounds of formula I described above for use as therapeutically active substances are a further object of the invention.

The compounds described above can be used for the production of medicaments for the prophylaxis and therapy of illnesses which are caused by disorders associated with the NPY receptor, particularly for the production of medicaments for the prophylaxis and therapy of arthritis, diabetes and particularly eating disorders and obesity. The subject invention provides a pharmaceutical composition comprising a compound of formula I described above and a therapeutically inert carrier. A further embodiment combines the above pharmaceutical composition with a therapeutically effective amount of a lipase inhibitor. A preferred lipase inhibitor is orlistat.

The subject compounds may be used in the production of medicaments, particularly for the treatment and prophylaxis of arthritis, diabetes and particularly eating disorders and obesity. A method for the treatment and prophylaxis of arthritis, diabetes and particularly eating disorders and obesity whereby an effective amount of a compound described above is administered, is described.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Assay Procedures

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase (Stratagene). The amplification product was subcloned into the mammalian expression vector pcDNA3 using Eco RI and XhoI restriction sites. Positive clones were sequenced and one clone, encoding the published sequence was selected for generation of stable cell clones.

Stable Transfection

Human embryonic kidney 293 (HEK293) cells were transfected with 10 µg mNPY5 DNA using the lipofectamine reagent (Gibco BRL) according to the manufacturer's instruction. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 µl 25 mM Hepes buffer (pH 7.4, 2.5 mM $CaCl_2$, 1 mM $MgCl_2$, 1% bovine serum albumine, and 0.01% $NaN_3$ containing 5 µg protein, 100 pM [$^{125}$I]labelled peptide YY (PYY) and 10 µL DMSO containing increasing amounts of unlabelled test compounds. After incubation for 1 h at 22° C., bound and free ligand are separated by filtration over glass fiber filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}I$] labelled neuropeptide Y. It is determined by linear regression analysis after logit/log transformation of the binding data.

Results obtained in the foregoing test using representative compounds of the invention as the test compounds are shown in the following table:

| Compound | $IC_{50}$ |
|---|---|
| 20 | 18 nM |
| 43 | 30 nM |

Preferred compounds as described above have $IC_{50}$ values below 1000 nM; more preferred compounds have $IC_{50}$ values below 100 nM, particularly below 10 nM. Most preferred compounds have $IC_{50}$ values below 1 nM. These results have been obtained by using the foregoing test.

The compounds of formula I and their pharmaceutically usable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically usable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts and esters can be used for the prophylaxis and treatment of arthritis, diabetes and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Preparation of the Compounds of Examples 1–11 can be Achieved as Follows:

General procedure for the condensation of 2,4-dimethyl-6-[dialkylamino]-pyrimidines with aromatic aldehydes A mixture of the pyrimidine derivative (1 mmol) and the aromatic aldehyde (1.0–1.5 mmol) was heated to reflux in propionic anhydride (0.4 ml) until the aldehyde had completely reacted (2–8 h). After cooling, the solution was diluted with ether, washed with 2 M aqueous NaOH solution and brine, dried ($MgSO_4$), and evaporated. The regioisomers were isolated by $SiO_2$ chromatography using a cycloyexane-ether gradient. Accordingly there were prepared:

Examples 1 and 2

On reaction of 2,4-dimethyl-6-pyrrolidin-1-yl-pyrimidine (J. Org. Chem. 1987, 52, 1017; 200 mg, 1.13 mmol) with 3-trifluoromethylbenzaldehyde (196 mg, 1.13 mmol): (E)-2-Methyl-4-pyrrolidin-1-yl-6-[2-(3-trifluoromethyl-phenyl)-vinyl]-pyrimidine (59 mg, 16%) as an off-white solid. ISP mass spectrum, m/e: 334.2 (M+1 calculated for $C_{18}H_{18}F_3N_3$: 334).

(E)-4-methyl-6-pyrrolidin-1-yl-2-[2-(3-trifluoromethyl-phenyl)-vinyl]-pyrimidine (33 mg, 9%) as a white solid. ISP mass spectrum, m/e: 334.3 (M+1 calculated for $C_{18}H_{18}F_3N_3$: 334).

Examples 3 and 4

On reaction of 2,4-dimethyl-6-piperidin-1-yl-pyrimidine (J. Org. Ghem. 1987, 52, 1017; 221 mg, 1.15 mmol) with 3-trifluoromethylbenzaldehyde (231 mg, 1.33 mmol): (E)-2-Methyl-4-piperidin-1-yl-6-[2-(3-trifluoromethyl-phenyl)-vinyl]-pyrimidine (147 mg, 37%) as a light yellow oil. ISP mass spectrum, m/e: 348.4 (M+1 calculated for $C_{19}H_{20}F_3N_3$: 348).

(E)-4-methyl-6-piperidin-1-yl-2-[2-(3-trifluoromethyl-phenyl)-vinyl]-pyrimidine (33 mg, 8%) as a light yellow oil. ISP mass spectrum, m/e: 348.4 (M+1 calculated for $C_{19}H_{20}F_3N_3$: 348).

Examples 5 and 6

On reaction of 4-(2,6-dimethyl-pyrimidin-4-yl)-morpholine (J. Org. Chem. 1987,52, 1017; 200 mg, 1.03 mmol) and 3-trifluoromethylbenzaldehyde (270 mg, 1.55 mmol): (E)-4-{2-Methyl-6-[2-(3-trifluoromethyl-phenyl)-vinyl]-pyrimidin-4-yl}-morpholine (58 mg, 16%) as an off-white solid. ISP mass spectrum, m/e: 350.3 (M+1 calculated for $C_{18}H_{18}F_3N_3O$: 350).

(E)-4-{6-methyl-2-[2-(3-trifluoromethyl-phenyl)-vinyl]-pyrimidin-4-yl}-morpholine (54 mg, 15%), as an off-white solid. ISP mass spectrum, m/e: 350.3 (M+1 calculated for $C_{18}H_{18}F_3N_3O$: 350).

Examples 7 and 8 a) On reaction of 2-(2,6-dimethyl-pyrimidin-4-yl)-1,2,3,4-tetrahydro-isoquinoline (200 mg, 0.836 mmol) with 3-trifluoromethylbenzaldehyde (167 mg, 0.961 mmol): (E)-2-{2-Methyl-6-[2-(3-trifluoromethyl-phenyl)-vinyl]-pyrimidin-4-yl}-1,2,3,4-tetrahydro-isoquinoline (132 mg, 40%) as a yellow oil. ISP mass spectrum, m/e: 396.3 (M+1 calculated for $C_{23}H_{20}F_3N_3$: 396).

(E)-2-{6-methyl-2-[2-(3-trifluoromethyl-phenyl)-vinyl]-pyrimidin-4-yl}-1,2,3,4-tetrahydro-isoquinoline (58 mg, 18%) as a yellow oil. ISP mass spectrum, m/e: 396.3 (M+1 calculated for $C_{23}H_{20}F_3N_3$: 396).

Preparation of the Starting Material:

b) A mixture of 4-chloro-2,6-dimethylpyrimidine (Chem. Ber. 1902, 35, 1575; 1.24 g, 8.70 mmol) and 1,2,3,4-tetrahydroisoquinoline (3.47 g, 26.1 mmol) was stirred at room temperature for 3 h. The solid formed was then dissolved in toluene (15 ml) and 1 M aqueous potassium phosphate buffer (pH 6.85, 15 ml). The organic layer was separated, washed with brine, dried ($MgSO_4$), and evaporated. Recrystallization in hexane (150 ml) yielded 2-(2,6-dimethyl-pyrimidin-4-yl)-1,2,3,4-tetrahydro-isoquinoline (1.71 g, 82%) as a crystalline light yellow solid. EI mass spectrum, m/e: 239.1 (M calculated for $C_{15}H_{17}N_3$: 239).

Example 9

On reaction of 2,4-dimethyl-6-pyrrolidin-1-yl-pyrimidine (J. Org. Chem. 1987, 52, 1017; 200 mg, 1.13 mmol) with 3-nitrobenzaldehyde (196 mg, 1.30 mmol): (E)-2-Methyl-4-[2-(3-nitro-phenyl)-vinyl]-6-pyrrolidin-1-yl-pyrimidine) (41 mg, 12%) as a yellow solid. EI mass spectrum, m/e: 310.1 (M calculated for $C_{17}H_{18}N_4O_2$: 310).

Examples 10 and 11

On reaction of 2,4-dimethyl-6-piperidin-1-yl-pyrimidine (J. Org. Chem. 1987, 52, 1017; 200 mg, 1.05 mmol) and 3-nitrobenzaldehyde (182 mg, 1.20 mmol): (E)-2-Methyl-4-[2-(3-nitro-phenyl)-vinyl]-6-piperidin-1-yl-pyrimidine (30 mg, 9%) as a yellow solid. ISP mass spectrum, m/e: 325.4 (M+1 calculated for $C_{23}H_{20}F_3N_3$: 325). (E)-4-methyl-2-[2-(3-nitro-phenyl)-vinyl]-6-piperidin-1-yl-pyrimidine (22 mg, 6%) as a yellow solid. ISP mass spectrum, m/e: 325.4 (M+1 calculated for $C_{23}H_{20}F_3N_3$: 325).

Example 12 a) A mixture of 66 mg (0.25 mmol) of (E) 4-chloro-2-[2-(3-chloro-phenyl)-vinyl]-6-methyl-pyrimidine and 0.89 g (12.5 mmol) pyrrolidine was heated at 60° C. for 1.5 h after which time the reaction was completed according to TLC analysis ($CH_2Cl_2$/EtOAc: 4/1). The excess pyrrolidine was removed in vacuo and the residue was purified on a silica gel chromatography column (eluted with $CH_2Cl_2$/EtOAc: 4/1). The purified fractions were combined, evacuated in vacuo, the solid residue was triturated with ether and filtered off by suction to give (E)-2-[2-(3-Chloro-phenyl)-vinyl]-4-methyl-6-pyrrolidin-1-yl-pyrimidine (61 mg, 80%) as an off-white crystalline solid. ISP mass spectrum, m/e: 300.3 (M+1 calculated for $C_{17}H_{18}ClN_3$: 300).

Preparation of the Starting Material:

b) 1.24 g (10 mmol) of 2,4-dimethyl-6-hydroxypyrimidine in acetic anhydride (2.8 ml) were treated at RT with 1.41 g (10 mmol) of 3-chlorobenzaldehyde and the mixture was heated for 5 hours at 145° C. until completion of the reaction according to TLC analysis. The reaction mixture was cooled to RT, the crystalline solid which had formed was filtered off by suction and washed with diethyl ether to give 1.92 g (78%) of the desired (E)-2-[2-(3-chloro-phenyl)-vinyl]-6-methyl-pyrimidin-4-ol as off-white crystals. EI mass spectrum, m/e: 246.1 (M calculated for $C_{13}H_{11}ClN_2O$: 246).

c) 0.246 g (1 mmol) of (E)-2-[2-(3-chloro-phenyl)-vinyl]-6-methyl-pyrimidin-4-ol were treated with 1.83 ml (20 mmol) of $POCl_3$ and subsequently heated at 130° C. for 4.5 hours. The mixture was cooled to RT, concentrated in vacuo and the residue was partitioned between EtOAc, water and saturated $KHCO_3$. The organic layer was separated, dried over sodium sulphate and concentrated in vacuo. The residue was applied to a short silica gel column with $CH_2Cl_2$/hexane (3:2) as eluent. Combination of the purified fractions and concentration in vacuo gave 188 mg (71%) of the desired (E)-4-chloro-2-[2-(3-chloro-phenyl)-vinyl]-6-methyl-pyrimidine as a white solid. EI mass spectrum, m/e: 264 (M calculated for $C_{13}H_{10}Cl_2N_2$: 264)

Example 13 a) In analogy to example 12a) from (E)-4-chloro-6-methyl-2-(2-thiophen-2-yl-vinyl)-pyrimidine (71 mg, 0.3 mmol) and pyrrolidine (1.24 ml, 15 mmol) there was obtained (E)-4-methyl-6-pyrrolidin-1-yl-2-(2-thiophen-2-yl-vinyl)-pyrimidine (55 mg, 66.7%) as an off-white crystalline solid. EI mass spectrum, m/e: 271 (M calculated for $C_{15}H_{17}N_3S$: 271).

Preparation of the Starting Material:

b) In analogy to example 12b), from 2,4-dimethyl-6-hydroxypyrimidine (1.24 g, 10 mmol) and 2-thiphenecarboxaldeyde (1.12 g, 10 mmol) in acetic anhydride there was obtained (E)-6-methyl-2-(2-thiophen-2-yl-vinyl)-pyrimidin-4-ol (0.51 g, 23%) as a yellow solid. EI mass spectrum, m/e: 218.1 (M calculated for $C_{11}H_{10}N_2OS$: 218).

c) In analogy to example 12c), by heating (E)-6-methyl-2-(2-thiophen-2-yl-vinyl)-pyrimidin-4-ol (0.38 g, 1.74 mmol) in $POCl_3$ (3.19 ml, 34.8 mmol) at 130° C. for 4.5 h was obtained (E)-4-chloro-6-methyl-2-(2-thiophen-2-yl-vinyl)-pyrimidine (0.236 g, 57%) as a light yellow solid. EI mass spectrum, m/e: 236 (M calculated for $C_{11}H_9ClN_2S$: 236).

Example 14 a) In analogy to example 12a) from (E)-4-chloro-2-[2-(4-methoxy-phenyl)-vinyl]-6-methyl-pyrimidine (78 mg, 0.3 mmol) and pyrrolidine (1.24 ml, 15 mmol) there was obtained (E)-2-[2-(4-methoxy-phenyl)-vinyl]-4-methyl-6-pyrrolidin-1-yl-pyrimidine (58 mg, 66.7%) as an off-white crystalline solid. ISP mass spectrum, m/e: 296.4 (M+1 calculated for $C_{18}H_{21}N_3O$: 296).

Preparation of the Starting Material:

b) In analogy to example 12b), from 2,4-dimethyl-6-hydroxypyrimidine (1.24 g, 10 mmol) and 4-methoxybenzaldehyde (1.36 g, 10 mmol) in acetic anhydride there was obtained (E)-2-[2-(4-methoxy-phenyl)-vinyl]-6-methyl-pyrimidin-4-ol (0.304 g, 12.5%) as a yellow solid. EI mass spectrum, m/e: 242.1 (M calculated for $C_{14}H_{14}N_2O_2$: 242).

c) In analogy to example 12c), by heating (E)-2-[2-(4-methoxy-phenyl)-vinyl]-6-methyl-pyrimidin-4-ol (0.3 g, 1.24 mmol) in $POCl_3$ (2.27 ml, 24.76 mmol) at 130° C. for 4.5 h there was obtained (E)-4-chloro-2-[2-(4-methoxy-phenyl)-vinyl]-6-methyl-pyrimidine (0.306 g, 94%) as a light yellow solid. EI mass spectrum, m/e: 260.1 (M calculated for $C_{14}H_{13}ClN_2O$: 260).

Example 15 a) In analogy to example 12a) from (E)-4-chloro-2-[2-(2,4-dimethoxy-phenyl)-vinyl]-6-methyl-pyrimidine (87.2 mg, 0.3 mmol) and pyrrolidine (1.24 ml, 15 mmol) there was obtained (E)-2-[2-(2,4-dimethoxy-phenyl)-vinyl]-4-methyl-6-pyrrolidin-1-yl-pyrimidine (58 mg, 60%) as an off-white crystalline solid. ISP mass spectrum, m/e: 326.4 (M+1 calculated for $C_{19}H_{23}N_3O_2$: 326).

Preparation of the Starting Material:

b) In analogy to example 12b), from 2,4-dimethyl-6-hydroxypyrimidine (1.86 g, 15 mmol) and 2,4-dimethoxybenzaldehyde (2.7 g, 15 mmol) in acetic anhydride there was obtained (E)-2-[2-(2,4-dimethoxy-phenyl)-vinyl]-6-methyl-pyrimidin-4-ol (0.864 g, 21%) as a yellow solid. EI mass spectrum, m/e: 272.1 (M calculated for $C_{15}H_{16}N_2O_3$: 272).

c) In analogy to example 12c), by heating (E)-2-[2-(2,4-dimethoxy-phenyl)-vinyl]-6-methyl-pyrimidin-4-ol (0.33 g, 1.22 mmol) in $POCl_3$ (2.24 ml, 24.5 mmol) at 130° C. for 4.5 h there was obtained 4-chloro-2-[2-(2,4-dimethoxy-phenyl)-vinyl]-6-methyl-pyrimidine (0.21 g, 60%) as a light yellow solid. EI mass spectrum, m/e: 290 (M calculated for $C_{15}H_{15}ClN_2O_2$: 290).

Example 16 a) In analogy to example 12a) from (E)-4-[2-(4-chloro-6-methyl-pyrimidin-2-yl)-vinyl]-benzonitrile (102 mg, 0.4 mmol) and pyrrolidine (1.65 ml, 20 mmol) there was obtained (E)-4-[2-(4-methyl-6-pyrrolidin-1-yl-pyrimidin-2-yl)-vinyl]-benzonitrile (98 mg, 85%) as a light yellow crystalline solid. ISP mass spectrum, m/e: 291.3 (M+1 calculated for $C_{18}H_{18}N_4$: 291).

Preparation of the Starting Material:

b) In analogy to example 12b), from 2,4-dimethyl-6-hydroxypyrimidine (1.24 g, 10 mmol) and 4-cyanobenzaldehyde (1.31 g, 10 mmol) in acetic anhydride there was obtained (E)-4-[2-(4-hydroxy-6-methyl-pyrimidin-2-yl)-vinyl]-benzonitrile (2.13 g, 90%) as a light yellow solid. EI mass spectrum, m/e: 237.1 (M calculated for $C_{14}H_{11}N_3O$: 237).

c) In analogy to example 12c), by heating (E)-4-[2-(4-hydroxy-6-methyl-pyrimidin-2-yl)-vinyl]-benzonitrile (0.71 g, 3 mmol) in $POCl_3$ (5.49 ml, 60 mmol) at 130° C. for 4.5 h there was obtained (E)-4-[2-(4-chloro-6-methyl-pyrimidin-2-yl)-vinyl]-benzonitrile (0.59 g, 76%) as a pink solid. EI mass spectrum, m/e: 255 (M calculated for $C_{14}H_{10}ClN_3$: 255).

Example 17 a) In analogy to example 12a) from (E)-4-chloro-2-[2-(3,4-dichloro-phenyl)-vinyl]-6-methyl-pyrimidine (74.9 mg, 0.25 mmol) and pyrrolidine (1.03 ml, 12.5 mmol) there was obtained (E)-2-[2-(3,4-dichloro-phenyl)-vinyl]-4-methyl-6-pyrrolidin-1-yl-pyrimidine (55 mg, 60%) as an off-white crystalline solid. ISP mass spectrum, m/e: 334.2 (M+1 calculated for $C_{17}H_{17}Cl_2N_3$: 334).

Preparation of the Starting Material:

b) In analogy to example 12b), from 2,4-dimethyl-6-hydroxypyrimidine (1.24 g, 10 mmol) and 3,4-dichloroybenzaldehyde (1.75 g, 10 mmol) in acetic anhydride there was obtained (E)-2-[2-(3,4-dichloro-phenyl)-vinyl]-6-methyl-pyrimidin-4-ol (1.96 g, 70%) as a light yellow solid. EI mass spectrum, m/e: 280 (M calculated for $C_{13}H_{10}Cl_2N_2O$: 280).

c) In analogy to example 12c), by heating (E)-2-[2-(3,4-dichloro-phenyl)-vinyl]-6-methyl-pyrimidin-4-ol (0.56 g, 2 mmol) in $POCl_3$ (3.66 ml, 40 mmol) at 130° C. for 4.5 h there was obtained (E)-4-chloro-2-[2-(3,4-dichloro-phenyl)-vinyl]-6-methyl-pyrimidine (0.345 g, 58%) as a pink solid. EI mass spectrum, m/e: 298 (M calculated for $C_{13}H_9Cl_3N_2$: 298).

Example 18 a) In analogy to example 12a) from 4-chloro-2-[2-(2,4-dichloro-phenyl)-vinyl]-6-methyl-pyrimidine (60 mg, 0.2 mmol) and pyrrolidine (0.83 ml, 10 mmol) there was obtained 2-[2-(2,4-dichloro-phenyl)-vinyl]-4-methyl-6-pyrrolidin-1-yl-pyrimidine (48 mg, 70%) as an off-white crystalline solid. ISP mass spectrum, m/e: 334.2 (M+1 calculated for $C_{17}H_{17}Cl_2N_3$: 334).

Preparation of the Starting Material:

b) In analogy to example 12b), from 2,4-dimethyl-6-hydroxypyrimidine (1.24 g, 10 mmol) and 2,4-dichlorobenzaldehyde (1.75 g, 10 mmol) in acetic anhydride there was obtained (E)-2-[2-(2,4-dichloro-phenyl)-vinyl]-6-methyl-pyrimidin-4-ol (2.08 g, 74%) as a light yellow solid. EI mass spectrum, m/e: 280 (M calculated for $C_{13}H_{10}Cl_2N_2O$: 280).

c) In analogy to example 12c), by heating (E)-2-[2-(2,4-dichloro-phenyl)-vinyl]-6-methyl-pyrimidin-4-ol (0.5 g, 1.78 mmol) in $POCl_3$ (3.26 ml, 35.6 mmol) at 130° C. for 4.5 h there was obtained (E)-4-chloro-2-[2-(2,4-dichloro-phenyl)-vinyl]-6-methyl-pyrimidine (0.491 g, 92%) as a pink solid. EI mass spectrum, m/e: 298 (M calculated for $C_{13}H_9Cl_3N_2$: 298).

Example 19

In analogy to example 12 from (E)-4-chloro-2-[2-(2,4-dichloro-phenyl)-vinyl]-6-methyl-pyrimidine (60 mg, 0.2 mmol), product of example 18c), and cyclopropylamine (0.7 ml, 10 mmol) there was obtained (E)-cyclopropyl-{2-[2-(2,4-dichloro-phenyl)-vinyl]-6-methyl-pyrimidin-4-yl}-amine (40 mg, 60%) as a white crystalline solid. ISP mass spectrum, m/e: 320.3 (M+1 calculated for $C_{17}H_{17}Cl_2N_3$: 320).

Example 20 a) In analogy to example 12a) from (E)-3-[2-(4-chloro-6-methyl-pyrimidin-2-yl)-vinyl]-benzonitrile (100 mg, 0.39 mmol) and pyrrolidine (2 ml, 24 mmol) there was obtained (E)-3-[2-(4-methyl-6-pyrrolidin-1-yl-pyrimidin-2-yl)-vinyl]-benzonitrile (81 mg, 72%) as a crystalline solid. ISP mass spectrum, m/e: 291.3 (M+1 calculated for $C_{18}H_{18}N_4$: 291).

Preparation of the Starting Material:

b) In analogy to example 12b), from 2,4-dimethyl-6-hydroxypyrimidine (1.1 g, 8.86 mmol) and 3-cyanobenzaldehyde (1.16 g, 8.86 mmol) in acetic anhydride there was obtained (E)-3-[2-(4-hydroxy-6-methyl-pyrimidin-2-yl)-vinyl]-benzonitrile (1.56 g, 74%) as a yellow solid. EI mass spectrum, m/e: 237 (M calculated for $C_{14}H_{11}N_3O$: 237).

c) In analogy to example 12c), by heating (E)-3-[2-(4-hydroxy-6-methyl-pyrimidin-2-yl)-vinyl]-benzonitrile (1 g, 4.21 mmol) in $POCl_3$ (7.7 ml, 84.3 mmol) at 130° C. for 4.5 h there was obtained (E)-3-[2-(4-chloro-6-methyl-pyrimidin-2-yl)-vinyl]-benzonitrile (1.07 g, 99%) as an orange solid. EI mass spectrum, m/e: 255 (M calculated for $C_{14}H_{10}ClN_3$: 255).

Example 21

In analogy to example 12 from (E)-3-[2-(4-chloro-6-methyl-pyrimidin-2-yl)-vinyl]-benzonitrile (100 mg, 0.39 mmol), product of example 20c), and cyclopropylamine (2 ml, 28.6 mmol) there was obtained (E)-3-[2-(4-cyclopropylamino-6-methyl-pyrimidin-2-yl)-vinyl]-benzonitrile (86 mg, 80%) as an off-white amorphous solid. ISP mass spectrum, m/e: 277.3 (M+1 calculated for $C_{17}H_{16}N_4$: 277).

Example 22

In analogy to example 12 from (E)-4-chloro-2-[2-(3-chloro-phenyl)-vinyl]-6-methyl-pyrimidine (50 mg, 0.19 mmol), product of example 12c), and cyclopropylamine (2 ml, 28.6 mmol) there was obtained (E)-{2-[2-(3-chloro-phenyl)-vinyl]-6-methyl-pyrimidin-4-yl}-cyclopropyl-amine (35 mg, 63%) as an off-white amorphous solid. ISP mass spectrum, m/e: 286.2 (M+1 calculated for $C_{16}H_{16}ClN_3$: 286).

Example 23

In analogy to example 12 from (E)-3-[2-(4-chloro-6-methyl-pyrimidin-2-yl)-vinyl]-benzonitrile (100 mg, 0.39 mmol), product of example 20c), and aminomethylcyclopropane (2 ml, 23.3 mmol) there was obtained under aminomethylcyclopropyl rearrangement (E)-3-{2-[4-(3-methyl-azetidin-1-yl)-6-methyl-pyrimidin-2-yl]-vinyl}-benzonitrile (80 mg, 72%) as an off-white amorphous solid. ISP mass spectrum, m/e: 291.3 (M+1 calculated for $C_{18}H_{18}N_4$: 291).

Example 24

In analogy to example 12 from (E)-4-chloro-2-[2-(3-chloro-phenyl)-vinyl]-6-methyl-pyrimidine (50 mg, 0.19 mmol), product of example 12c), and aminomethyl-cyclopropane (2 ml, 23.3 mmol) there was obtained under aminomethylcyclopropyl rearrangement (E)-2-[2-(3-chloro-phenyl)-vinyl]-4-methyl-6-(3-methyl-azetidin-1-yl)-pyrimidine (37 mg, 63%) as a white amorphous solid. ISP mass spectrum, m/e: 300.2 (M+1 calculated for $C_{17}H_{18}ClN_3$: 300).

Example 25

In analogy to example 12 from (E)-3-[2-(4-chloro-6-methyl-pyrimidin-2-yl)-vinyl]-benzonitrile (100 mg, 0.39 mmol), product of example 20c), and 3-hydroxy-pyrrolidine (2 ml, 21.3 mmol) there was obtained (E)-3-{2-[4-(3-hydroxy-pyrrolidin-1-yl)-6-methyl-pyrimidin-2-yl]-vinyl}-benzonitrile (86 mg, 96%) as a light yellow solid. ISP mass spectrum, m/e: 307.3 (M+1 calculated for $C_{18}H_{18}N_4O$: 307).

Example 26

In analogy to example 12 from (E)-3-[2-(4-chloro-6-methyl-pyrimidin-2-yl)-vinyl]-benzonitrile (100 mg, 0.39 mmol), product of example 20 c), and butylamine (2 ml, 21.3 mmol) there was obtained (E)-3-[2-(4-butylamino-6-methyl-pyrimidin-2-yl)-vinyl]-benzonitrile (82 mg, 72%) as a an amorphous off-white solid. ISP mass spectrum, m/e: 293.3 (M+1 calculated for $C_{18}H_{20}N_4$: 293).

Example 27 a) In analogy to example 12a) from (E)-4-chloro-2-[2-(4-dimethylamino-phenyl)-vinyl]-6-methyl-pyrimidine (100 mg, 0.37 mmol) and pyrrolidine (2 ml, 24 mmol) there was obtained (E)-dimethyl-{4-[2-(4-methyl-6-pyrrolidin-1-yl-pyrimidin-2-yl)-vinyl]-phenyl}-amine (19 mg, 16.8%) as a yellow amorphous solid. ISP mass spectrum, m/e: 309.2 (M+1 calculated for $C_{19}H_{24}N_4$: 309).

Preparation of the Starting Material:

b) In analogy to example 12b), from 2,4-dimethyl-6-hydroxypyrimidine (1.5 g, 12 mmol) and 4-dimethylaminobenzaldehyde (1.8 g, 12 mmol) in acetic anhydride there was obtained (E)-2-[2-(4-dimethylamino-phenyl)-vinyl]-6-methyl-pyrimidin-4-ol (3.1 g) as a black oil which was used in the next reaction without further purification.

c) In analogy to example 12c), by heating 2-[2-(4-dimethylamino-phenyl)-vinyl]-6-methyl-pyrimidin-4-ol (2 g, 7.8 mmol) in $POCl_3$ (14.3 ml, 157 mmol) at 130° C. for 4.5 h there was obtained (E)-4-chloro-2-[2-(4-dimethylamino-phenyl)-vinyl]-6-methyl-pyrimidine (0.38 g, 18.5%) as a dark oil. EI mass spectrum, m/e: 273 (M calculated for $C_{15}H_{16}ClN_3$: 273).

Example 28 a) In analogy to example 12a) from (E)-2-(2-benzo[1,3]dioxol-5-yl-vinyl)-4-chloro-6-methyl-pyrimidine (60 mg, 0.22 mmol) and pyrrolidine (2 ml, 24 mmol) there was obtained (E)-2-(2-benzo [1,3]dioxol-5-yl-vinyl)-4-methyl-6-pyrrolidin-1-yl-pyrimidine (55 mg, 81%) as an off-white amorphous solid. ISP mass spectrum, m/e: 310.2 (M+1 calculated for $C_{18}H_{19}N_3O_2$: 310).

Preparation of the Starting Material:

b) In analogy to example 12b), from 2,4-dimethyl-6-hydroxypyrimidine (1.5 g, 12 mmol) and piperonal (1.8 g, 12 mmol) in acetic anhydride there was obtained (E)-2-(2-benzo[1,3]dioxol-5-yl-vinyl)-6-methyl-pyrimidin-4-ol (0.76 g, 24.5%) as a yellow solid. EI mass spectrum, m/e: 256 (M calculated for $C_{14}H_{14}N_2O_3$: 256).

c) In analogy to example 12c), by heating (E)-2-(2-benzo[1,3]dioxol-5-yl-vinyl)-6-methyl-pyrimidin-4-ol (0.5 g, 1.95 mmol) in $POCl_3$ (3.5 ml, 39 mmol) at 130° C. for 4.5 h there was obtained (E)-2-(2-benzo [1,3]dioxol-5-yl-vinyl)-4-chloro-6-methyl-pyrimidine (0.48 g, 90%) as a yellow solid. ISP mass spectrum, m/e: 275.2 (M+1 calculated for $C_{14}H_{11}Cl_2N_2$: 275).

Example 29 a) In analogy to example 12a) from (E)-4-chloro-2-[2-(3-methoxy-phenyl)-vinyl]-6-methyl-pyrimidine (60 mg, 0.22 mmol) and pyrrolidine (2 ml, 24 mmol) there was obtained (E)-2-[2-(3-methoxy-phenyl)-vinyl]-4-methyl-6-pyrrolidin-1-yl-pyrimidine (60 mg, 97%) as an off-white amorphous solid. ISP mass spectrum, m/e: 296.3 (M+1 calculated for $C_{18}H_{21}N_3O$: 296).

Preparation of the Starting Material:

b) In analogy to example 12b), from 2,4-dimethyl-6-hydroxypyrimidine (1.5 g, 12 mmol) and 3-methoxybenzaldehyde (1.6 g, 12 mmol) in acetic anhydride there was obtained (E)-2-[2-(3-methoxy-phenyl)-vinyl]-6-methyl-pyrimidin-4-ol (0.84 g, 29%) as a yellow solid. EI mass spectrum, m/e: 242 (M calculated for $C_{14}H_{14}N_2O_2$: 242).

c) In analogy to example 12c), by heating (E)-2-[2-(3-methoxy-phenyl)-vinyl]-6-methyl-pyrimidin-4-ol (0.6 g, 2.48 mmol) in $POCl_3$ (4.6 ml, 29.5 mmol) at 130° C. for 4.5 h there was obtained (E)-4-chloro-2-[2-(3-methoxy-phenyl)-vinyl]-6-methyl-pyrimidine (0.53 g, 82%) as an orange solid. ISP mass spectrum, m/e: 261.2 (M+1 calculated for $C_{14}H_{13}ClN_2O$: 261).

Example 30

In analogy to example 12 from (E)-4-chloro-2-[2-(3-methoxy-phenyl)-vinyl]-6-methyl-pyrimidine (60 mg, 0.23 mmol), product of example 29c), and (S)-3-ethoxy-pyrrolidine (132 mg, 1.1 mmol;)—preparation according to Tetrahedron Lett. 1995,2745—there was obtained (E),(S)-4-(3-ethoxy-pyrrolidin-1-yl)-2-[2-(3-methoxy-phenyl)-vinyl]-6-methyl-pyrimidine (71 mg, 91%) as a white amorpous solid. ISP mass spectrum, m/e: 340.3 (M+1 calculated for $C_{20}H_{25}N_3O_2$: 340).

Example 31

To a solution of (E)-2-[2-(3-methoxy-phenyl)-vinyl]-4-methyl-6-pyrrolidin-1-yl-pyrimidine (100 mg, 0.34 mmol), product of example 29, in $CH_2Cl_2$ there was added dropwise and under stirring at 0° C. a 1M solution of $BBr_3$ in $CH_2Cl_2$ (0.51 ml). The reaction mixture was stirred for 1 h at 0° C. after which time the reaction was complete according to TLC analysis. The mixture was poured on ice and the product extracted into $CH_2Cl_2$. The organic layer was dried over $Na_2SO_4$ and concentrated in vacuo. The crystalline solid which formed was filted off by suction and dried in a high vacuum to give (E)-2-[2-(3-hydroxy-phenyl)-vinyl]-4-methyl-6-pyrrolidin-1-yl-pyrimidine (45 mg, 47.2%) as a light grey solid. ISP mass spectrum, m/e: 282.2 (M+1 calculated for $C_{17}H_{19}N_3O$: 282).

Example 32

In analogy to example 12 from (E)-3-[2-(4-chloro-6-methyl-pyrimidin-2-yl)-vinyl]-benzonitrile (60 mg, 0.23 mmol) product of example 20c), and ethylendiamine there was obtained (E)-3-{2-[4-(2-amino-ethylamino)-6-methyl-pyrimidin-2-yl]-vinyl}-benzonitrile (36 mg, 55%) as an off-white solid. ISP mass spectrum, m/e: 280.2 (M+1 calculated for $C_{16}H_{17}N_5$: 280).

Example 33

In analogy to example 12 from (E)-3-[2-(4-chloro-6-methyl-pyrimidin-2-yl)-vinyl]-benzonitrile (60 mg, 0.24 mmol), product of example 20c), and (S)-3-ethoxy-pyrrolidine (135 mg, 1.2 mmol) there was obtained (E),(S)-3-{2-[4-(3-ethoxy-pyrrolidin-1-yl)-6-methyl-pyrimidin-2-yl]-vinyl}-benzonitrile (79 mg, 100%) as an off-white foam.ISP mass spectrum, m/e: 335.3 (M+1 calculated for $C_{20}H_{22}N_4O$: 335).

Example 34

A mixture of 100 mg (0.34 mmol) of (E)-3-[2-(4-methyl-6-pyrrolidin-1-yl-pyrimidin-2-yl)-vinyl]-benzonitrile, 448 mg (6.9 mmol) $NaN_3$ and 368 mg (6.9 mmol) $NH_4Cl$ in 10 ml DMF was heated at 70° C. for 20 h until completion of the reaction according to TLC analysis. The reaction mixture was cooled to RT, concentrated in vacuo and then partitioned between 1N HCl and $CH_2Cl_2$. The organic layer was separated and the aqueous layer extracted several times with $CH_2Cl_2$. The combined organic layers were dried over $Na_2SO_4$ and concentrated in vacuo. The crystalline solid which formed was filted off by suction and dried in a high vacuum to give ((E)-4-methyl-6-pyrrolidin-1-yl-2-{2-[3-(2H-tetrazol-5-yl)-phenyl]-vinyl}-pyrimidine (20 mg, 17.4%) as an off-white solid. ISP mass spectrum, m/e: 334.3 (M+1 calculated for $C_{18}H_{19}N_7$: 334).

Example 35 a) In analogy to example 12a) from (E)-4-chloro-6-methyl-2-[2-(4-methylsulfanyl-phenyl)-vinyl]-pyrimidine (300 mg, 0.22 mmol) and pyrrolidine (2 ml, 24 mmol) there was obtained (E)-4-methyl-2-[2-(4-methylsulfanyl-phenyl)-vinyl]-6-pyrrolidin-1-yl-pyrimidine (330 mg, 98%) as an off-white amorphous solid. ISP mass spectrum, m/e: 312.2 (M+1 calculated for $C_{18}H_{21}N_3S$: 312).

Preparation of the Starting Material:

b) In analogy to example 12b), from 2,4-dimethyl-6-hydroxypyrimidine (2 g, 16.1 mmol) and 4-methymercaptobenzaldehyde (2.45 g, 16.1 mmol) in acetic anhydride there was obtained (E)-6-methyl-2-[2-(4-methylsulfanyl-phenyl)-vinyl]-pyrimidin-4-ol (3.27 g, 78%) as a yellow solid. EI mass spectrum, m/e: 258.1 (M calculated for $C_{14}H_{14}N_2OS$: 258).

c) In analogy to example 12c), by heating (E)-6-methyl-2-[2-(4-methylsulfanyl-phenyl)-vinyl]-pyrimidin-4-ol (2 g, 7.74 mmol) in $POCl_3$ (14 ml, 0.15 mol) at 130° C. for 4.5 h there was obtained (E)-4-chloro-6-methyl-2-[2-(4-methylsulfanyl-phenyl)-vinyl]-pyrimidine (1.99 g, 93%) as an off-white solid. EI mass spectrum, m/e: 276.1 (M calculated for $C_{14}H_{13}ClN_2S$: 276).

Example 36

To a solution of 150 mg (0.48 mmol) of (E)-4-chloro-6-methyl-2-[2-(4-methyl-sulfanyl-phenyl)-vinyl]-pyrimidine, product of example 35, in 10 ml $CH_2Cl_2$ were added at 0° C. 356 mg (1.44 mmol) m-chloroperbenzoic acid and the mixture was then stirred at RT for 2 h until completion of the reaction according to TLC analysis. The reaction mixture was partitioned between cold aqueous $KHCO_3$ and $CH_2Cl_2$, the layers were separated and the aqueous layer twice extracted with $CH_2Cl_2$. The combined organic layers were tried over $Na_2SO_4$ and concentrated in vacuo. The residue was applied to a silica gel column with MeOH/$CH_2Cl_2$ (gradient: 2%–30%) as eluent. Combination of the purified fractions and concentration in vacuo gave the desired 2-[2-(4-methanesulfonyl-phenyl)-vinyl]-4-methyl-6-pyrrolidin-1-yl-pyrimidine as an (E/Z)-mixture (1/1) in amorphous, off-white form. ISP mass spectrum, m/e: 344.3 (M+1 calculated for C18H21N3OS: 344).

Example 37 a) In analogy to example 12a) from (E)-4-chloro-6-methyl-2-[2-(3-fluoro-phenyl)-vinyl]-pyrimidine (100 mg, 0.4 mmol) and pyrrolidine (1.65 ml, 20 mmol) there was obtained (E)-2-[2-(3-fluoro-phenyl)-vinyl]-4-methyl-6-pyrrolidin-1-yl-pyrimidine (110 mg, 98%) as an off-white amorphous solid. ISP mass spectrum, m/e: 284.2 (M+1 calculated for $C_{17}H_{18}FN_3$: 284).

Preparation of the Starting Material:

b) In analogy to example 12b), from 2,4-dimethyl-6-hydroxypyrimidine (1.24 g, 10 mmol) and 3-fluorobenzaldehyde (1.24 g, 10 mmol) in acetic anhydride there was obtained (E)-6-methyl-2-[2-(3-fluoro-phenyl)-vinyl]-pyrimidin-4-ol (1.22 g, 53%) as a light-yellow solid. EI mass spectrum, m/e: 230.1 (M calculated for $C_{13}H_{11}FN_2O$: 230).

c) In analogy to example 12c), by heating (E)-6-methyl-2-[2-(3-fluoro-phenyl)-vinyl]-pyrimidin-4-ol 1 (1.12 g, 4.86 mmol) in $POCl_3$ (9 ml, 0.1 mol) at 130° C. for 4.5 h there was obtained (E)-4-chloro-6-methyl-2-[2-(3-fluoro-phenyl)-vinyl]-pyrimidine (1 g, 86%) as a white solid. EI mass spectrum, m/e: 248 (M calculated for $C_{14}H_{13}ClFN_2$: 248).

Example 38

In analogy to example 12 from (E)-4-chloro-6-methyl-2-[2-(3-fluoro-phenyl)-vinyl]-pyrimidine (100 mg, 0.4 mmol), product of example 37c), and (S)-3-ethoxy-pyrrolidine (230 mg, 2 mmol) in dioxane (2 ml) there was obtained (E),(S)-

4-(3-ethoxy-pyrrolidin-1-yl)-2-[2-(3-fluoro-phenyl)-vinyl]-6-methyl-pyrimidine (90 mg, 70%) as an colorless liquid. ISP mass spectrum, m/e: 328.3 (M+1 calculated for $C_{19}H_{22}FN_3O$: 328).

Example 39 a) In analogy to example 12a) from (E)-2-[2-(3-benzyloxy-phenyl)-vinyl]-4-chloro-6-methyl-pyrimidine (500 mg, 1.5 mmol) and pyrrolidine (2 ml, 25 mmol) there was obtained ((E)-2-[2-(3-benzyloxy-phenyl)-vinyl]-4-methyl-6-pyrrolidin-1-yl-pyrimidine (250 mg, 46%) as an off-white solid. ISP mass spectrum, m/e: 372.3 (M+1 calculated for $C_{24}H_{25}N_3O$: 372).
Preparation of the Starting Material:

b) In analogy to example 12b), from 2,4-dimethyl-6-hydroxypyrimidine (2 g, 16.1 mmol) and 3-benzyloxybenzaldehyde (3.42 g, 16.1 mmol) in acetic anhydride there was obtained (E)-2-[2-(3-benzyloxy-phenyl)-vinyl]-6-methyl-pyrimidin-4-ol (2.8 g, 54%) as a off-white solid. EI mass spectrum, m/e: 318 (M calculated for $C_{20}H_{18}N_2O_2$: 318).

c) In analogy to example 12c), by heating (E)-2-[2-(3-benzyloxy-phenyl)-vinyl]-6-methyl-pyrimidin-4-ol (1.5 g, 4.7 mmol) in $POCl_3$ (8.65ml, 0.094 mol) at 130° C. for 4.5 h there was (E)-2-[2-(3-benzyloxy-phenyl)-vinyl]-4-chloro-6-methyl-pyrimidine (1 g, 86%) as a light-yellow solid. EI mass spectrum, m/e: 336 (M calculated for $C_{20}H_{17}ClN_2O$: 336).

Example 40 a) In analogy to example 12a) from (E)-3-[2-(4-chloro-6-methyl-pyrimidin-2-yl)-vinyl]-benzoic acid methyl ester (120 mg, 0.42 mmol) and pyrrolidine (60 mg, 0.83 mmol) there was obtained (E)-3-[2-(4-methyl-6-pyrrolidin-1-yl-pyrimidin-2-yl)-vinyl]-benzoic acid methyl ester (120 mg, 92%) as an light-yellow solid. ISP mass spectrum, m/e: 324.4 (M+1 calculated for $C_{19}H_{21}N_3O_2$: 324).
Preparation of the Starting Material:

b) In analogy to example 12b), from 2,4-dimethyl-6-hydroxypyrimidine (1.86 g, 15 mmol) and 3-methoxycarbonylbenzaldehyde (2.46 g, 15 mmol) in acetic anhydride there was obtained (E)-3-[2-(4-hydroxy-6-methyl-pyrimidin-2-yl)-vinyl]-benzoic acid methyl ester (3.16 g, 78%) as a yellow solid. ISN mass spectrum, m/e: 269.3 (M-H calculated for $C_{15}H_{14}N_2O_3$: 269).

c) In analogy to example 12c), by heating (E)-3-[2-(4-hydroxy-6-methyl-pyrimidin-2-yl)-vinyl]-benzoic acid methyl ester (2 g, 7.4 mmol) in $POCl_3$ (13.6 ml, 0.15 mol) at 130° C. for 4.5 h there was obtained (E)-3-[2-(4-chloro-6-methyl-pyrimidin-2-yl)-vinyl]-benzoic acid methyl ester (0.97 g, 45%) as a light-yellow solid. EI mass spectrum, m/e: 288.1 (M calculated for $C_{15}H_{13}ClN_2O_2$: 288).

Example 41

A solution of 60 mg of (E)-3-[2-(4-methyl-6-pyrrolidin-1-yl-pyrimidin-2-yl)-vinyl]-benzoic acid methyl ester, product of example 40, in MeOH/THF (each 2 ml) was treated at RT with 41 mg (0.37 mmol) $CaCl_2$ followed by 28 mg (0.74 mmol) $NaBH_4$ and then stirred for 18 h at RT until completion of the reaction according to TLC analysis. The reaction mixture was partitioned between diluted aqueous HCl and EtOAc. The organic layer was separated, dried over $Na_2SO_4$ and concentrated in vacuo. The residue was applied to a short silica gel column with $CH_2Cl_2$/MeOH (95/%) as eluent. Combination of the purified fractions and concentration in vacuo gave 10 mg (18%) of the desired (E){3-[2-(4-methyl-6-pyrrolidin-1-yl-pyrimidin-2-yl)-vinyl]-phenyl}-methanol as a white solid. ISP mass spectrum, m/e: 296.4 (M+1 calculated for $C_{18}H_{21}ClN_3O$: 296).

Example 42 a) In analogy to example 12a) from (E)-4-chloro-2-[2-(3,4-difluoro-phenyl)-vinyl]-6-methyl-pyrimidine (106 mg, 0.4 mmol) and pyrrolidine (1.65 ml, 20 mmol) there was obtained (E)-2-[2-(3,4-difluoro-phenyl)-vinyl]-4-methyl-6-pyrrolidin-1-yl-pyrimidine (60 mg, 37%) as an off-white solid. ISP mass spectrum, m/e: 302.3 (M+1 calculated for $C_{17}H_{17}F_2N_3$: 302)
Preparation of the Starting Material:

b) In analogy to example 12b), from 2,4-dimethyl-6-hydroxypyrimidine (1.24 g, 10 mmol) and 3,4-difluorobenzaldehyde (1.03 ml, 10 mmol) in acetic anhydride there was obtained 2-[2-(3,4-difluorofluoro-phenyl)-vinyl]-6-methyl-pyrimidin-4-ol (1.54 g, 62%) as a yellow solid. EI mass spectrum, m/e: 248 (M calculated for $C_{13}H_{10}F_2N_2O_2$: 248).

c) In analogy to example 12c), by heating obtained 2-[2-(3,4-difluoro-phenyl)-vinyl]-6-methyl-pyrimidin-4-ol (1.54 g, 6.2 mmol) in $POCl_3$ (11.83 ml, 0.12 mol) at 130° C. for 4.5 h there was obtained (E)-4-chloro-2-[2-(3,4-difluoro-phenyl)-vinyl]-6-methyl-pyrimidine (1.1 g, 66.5%) as a light-yellow solid. EI mass spectrum, m/e: 266 (M calculated for $C_{13}H_9F_2N_2Cl$: 266).

Example 43 a) In analogy to example 12a) from (E)-4-chloro-2-[2-(2,4-difluoro-phenyl)-vinyl]-6-methyl-pyrimidine (106 mg, 0.4 mmol) and pyrrolidine (1.65 ml, 20 mmol) there was obtained (E)-2-[2-(2,4-difluoro-phenyl)-vinyl]-4-methyl-6-pyrrolidin-1-yl-pyrimidine (60 mg, 37%) as an off-white solid. ISP mass spectrum, m/e: 302.2 (M+1 calculated for $C_{17}H_{17}F_2N_3$: 302).
Preparation of the Starting Material:

b) In analogy to example 12b), from 2,4-dimethyl-6-hydroxypyrimidine (1.24 g, 10 mmol) and 2,4-difluorobenzaldehyde (1.03 ml, 10 mmol) in acetic anhydride there was obtained (E)-2-[2-(2,4-difluorofluoro-phenyl)-vinyl]-6-methyl-pyrimidin-4-ol (1.48 g, 60%) as a white solid. EI mass spectrum, m/e: 248 (M calculated for $C_{13}H_{10}F_2N_2O_2$: 248).

c) In analogy to example 12c), by heating (E)-2-[2-(2,4-difluoro-phenyl)-vinyl]-6-methyl-pyrimidin-4-ol (1.48 g, 6 mmol) in $POCl_3$ (10.96 ml, 0.12 mol) at 130° C. for 4.5 h there was obtained (E)-4-chloro-2-[2-(3,4-difluoro-phenyl)-vinyl]-6-methyl-pyrimidine (1 g, 63%) as a yellow solid. EI mass spectrum, m/e: 266.1 (M calculated for $C_{13}H_9F_2N_2Cl$: 266).

Example 44 a) In analogy to example 12a) from (E)-4-chloro-2-[2-(3-chloro-4-fluoro-phenyl)-vinyl]-6-methyl-pyrimidine (80 mg, 0.3 mmol) and pyrrolidine (1.24 ml, 15 mmol) there was obtained (E)-2-[2-(3-chloro-4-fluoro-phenyl)-vinyl]-4-methyl-6-pyrrolidin-1-yl-pyrimidine (21 mg, 22%) as an yellow solid. ISP mass spectrum, m/e: 318.2 (M+1 calculated for $C_{17}H_{17}ClFN_3$: 318).
Preparation of the Starting Material:

b) In analogy to example 12b), from 2,4-dimethyl-6-hydroxypyrimidine (1.24 g, 10 mmol) and 3-chloro-4-fluorobenzaldehyde (1.58 g, 10 mmol) in acetic anhydride there was obtained (E)-2-[2-(3-chloro-4-fluorofluoro-phenyl)-vinyl]-6-methyl-pyrimidin-4-ol (2 g, 75%) as an off-white solid. EI mass spectrum, m/e: 264 (M calculated for $C_{13}H_{10}ClFN_2O$: 264).

c) In analogy to example 12c), by heating (E)-2-[2-(3-chloro-4-fluorofluoro-phenyl)-vinyl]-6-methyl-pyrimidin-4-ol (1.85 g, 7 mmol) in $POCl_3$ (12.83 ml, 0.14 mol) at 130° C. for 4.5 h there was obtained (E)-4-chloro-2-[2-(3-chloro-4-fluoro-phenyl)-vinyl]-6-methyl-pyrimidine (1.65 g, 83%) as a yellow solid. EI mass spectrum, m/e: 282 (M+1 calculated for $C_{13}H_9Cl_2FN_2$: 282).

Example 45 a) In analogy to example 12a) from (E)-3-[2-(4-chloro-6-methyl-pyrimidin-2-yl)-vinyl]-4-methoxy-N,N-dimethyl-benzenesulfonamide (147 mg, 0.4 mmol) and pyrrolidine (1.65 ml, 20 mmol) there was obtained (E)-4-methoxy-N,N-dimethyl-3-[2-(4-methyl-6-pyrrolidin-1-yl-pyrimidin-2-yl)-vinyl]-benzenesulfonamide (142 mg, 88%) as an off-white solid. ISP mass spectrum, m/e: 403.5 (M+1 calculated for $C_{20}H_{26}N_4O_3S$: 403).

Preparation of the Starting Material:

b) In analogy to example 12b), from 2,4-dimethyl-6-hydroxypyrimidine (1.02 g, 8.2 mmol) and 3-formyl-4-methoxy-N,N-dimethyl-benzenesulfonamide (2 g, 8.2 mmol) in acetic anhydride there was (E)-3-[2-(4-hydroxy-6-methyl-pyrimidin-2-yl)-vinyl]-4-methoxy-N,N-dimethyl-benzenesulfonamide (2 g, 69%) as an off-white solid. EI mass spectrum, m/e: 349 (M calculated for $C_{16}H_{19}N_3O_4S$: 349).

c) In analogy to example 12c), by (E)-3-[2-(4-hydroxy-6-methyl-pyrimidin-2-yl)-vinyl]-4-methoxy-N,N-dimethyl-benzenesulfonamide (2g, 5.7 mmol) in $POCl_3$ (10.48 ml, 0.11 mol) at 130° C. for 4.5 h there was obtained from (E)-3-[2-(4-chloro-6-methyl-pyrimidin-2-yl)-vinyl]-4-methoxy-N,N-dimethyl-benzenesulfonamide (1.43 g, 68%) as a yellow solid. EI mass spectrum, m/e: 367.1 (M calculated for $C_{16}H_{18}N_3O_3SCl$: 367).

Example 46 a) In analogy to example 12a) from (E)-4-chloro-2-[2-(3-nitro-phenyl)-vinyl]-6-methyl-pyrimidine (270 mg, 1 mmol) and pyrrolidine (4.34 ml, 52 mmol) there was obtained (E)-4-methyl-2-[2-(3-nitro-phenyl)-vinyl]-6-pyrrolidin-1-yl-pyrimidine (240 mg, 73.65%) as an yellow solid. ISP mass spectrum, m/e: 311.2 (M+1 calculated for $C_{17}H_{18}N_4O_2$: 311).

Preparation of the Starting Material:

b) In analogy to example 12b), from 2,4-dimethyl-6-hydroxypyrimidine (1.24 g, 10 mmol) and 3-nitro-benzaldehyde (1.5 g, 10 mmol) in acetic anhydride there was (E)-2-[2-(3-nitro-phenyl)-vinyl]-6-methyl-pyrimidin-4-ol (2.1 g, 84%) as an off-white solid.

c) In analogy to example 12c), by heating was (E)-2-[2-(3-nitro-phenyl)-vinyl]-6-methyl-pyrimidin-4-ol (1.28 g, 5 mmol) in $POCl_3$ (9.16 ml, 0.1 mol) at 130° C. for 4.5 h there was obtained (E)-4-chloro-2-[2-(3-nitro-phenyl)-vinyl]-6-methyl-pyrimidine (0.97 g, 71%) as an off-white solid. EI mass spectrum, m/e: 275 (M calculated for $C_{13}H_{10}ClN_3O_2$: 275).

Example 47

To a suspension of 480 mg (1.57 mmol) of (E)-4-methyl-2-[2-(3-nitro-phenyl)-vinyl]-6-pyrrolidin-1-yl-pyrimidine in 12 ml ethanol were added at RT 1.41 g (6.28 mmol) stannous chloride dihydrate followed by dropwise addition of 1 ml 36% HCl. The mixture was stirred at RT for 12 h, the pH adjusted to pH 7 by dropwise addition of 3N NaOH and then extracted several times with AcOEt. The organic layers were combined, dried over $Na_2SO_4$ and concentrated in vacuo. The residue was applied to a silica gel column with $CH_2Cl_2$/MeOH (10/1) as eluent. Combination of the purified fractions and evacuation in vacuo gave 289 mg (65.7%) of the desired (E)-3-[2-(4-methyl-6-pyrrolidin-1-yl-pyrimidin-2-yl)-vinyl]-phenylamine as a yellow solid. ISP mass spectrum, m/e: 281.2 (M+1 calculated for $C_{17}H_{20}N_4$: 281).

Example 48 a) In analogy to example 12a) from 4-chloro-2-[2-(3,5-dichloro-phenyl)-vinyl]-6-methyl-pyrimidine (200 mg, 0.67 mmol) and pyrrolidine (237 mg, 3.3 mmol) in isopropanol (2 ml) there was obtained (E)2-[2-(3,5-dichloro-phenyl)-vinyl]-4-methyl-6-pyrrolidin-1-yl-pyrimidine (193 mg, 86.5%) as light-brown solid. ISP mass spectrum, m/e: 334.2 (M+1 calculated for $C_{17}H_{17}Cl_2N_3$: 334).

Preparation of the Starting Material:

b) In analogy to example 12b), from 2,4-dimethyl-6-hydroxypyrimidine (2 g, 16.1 mmol) and 3,5-dichloro-benzaldehyde (2.8 g, 16 mmol) in acetic anhydride there was obtained 2-[2-(3,5-dichloro-phenyl)-vinyl]-6-methyl-pyrimidin-4-ol (4.24 g, 93%) as an light-red solid. ISP mass spectrum, m/e: 281.1 (M+1 calculated for $C_{13}H_{10}Cl2N_2O$: 281).

c) In analogy to example 12c), by heating 2-[2-(3,5-dichloro-phenyl)-vinyl]-6-methyl-pyrimidin-4-ol (3 g, 10.6 mmol) in $POCl_3$ (19.6 ml, 0.21 mol) at 130° C. for 4.5 h the obtained 4-chloro-2-[2-(3,5-dichloro-phenyl)-vinyl]-6-methyl-pyrimidine (2.74 g, 86%) as a light-red solid. EI mass spectrum, m/e: 298.1 (M calculated for $C_{13}H_9C_3N_2$: 298).

Example 49 a) To a stirred solution of 100 mg (0.5 mmol) of 2-chloro-4-methyl-6-pyrrolidin-1-yl-pyrimidine in 0.5 ml DMF under an argon atmosphere were added at RT 67 mg (0.25 mmol) tris-(o-tolyl)phosphine, 5.5 mg (0.025 mmol) palladium(II) acetate, 17 mg (0.2 mmol) $NaHCO_3$ followed by 263 mg (2.5 mmol) 2-vinylpyridine. The mixture was heated at 130° C. for 48 h, cooled to RT and 1.5 ml saturated aqueous NaCl solution was added. The mixture was extracted 4-times with 2 ml $EtOAc/Et_2O$ (2/1), the combined organic layers were washed with saturated aqueous NaCl, dried over $MgSO_4$ and concentrated in vacuo. The residue was applied to a silica gel column with hexane/EtOAc as eluent (gradient: 1/1 to 1/9). Combination of the purified fractions and concentration in vacuo gave 26 mg (20%) of the desired (E)-4-methyl-2-(2-pyridin-2-yl-vinyl)-6-pyrrolidin-1-yl-pyrimidine as yellow solid. ISP mass spectrum, m/e: 267.3 (M+1 calculated for $C_{16}H_{18}N_4$: 267).

Preparation of the Starting Material:

b) 0.815 g (5 mmol) of 2,4-dichloro-6-methylpyrimidine dissolved in in 5 ml isopropanol were treated under ice-cooling dropwise with 0.71 g (10 mmol) pyrrolidine. The mixture was stirred for 1 h at RT the concentrated in vacuo. The residue was purified on a silica gel chromatography column with $CH_2Cl_2$/AcOEt (4/1) as eluent to give 0.72 g (73%) of the desired 2-chloro-4-methyl-6-pyrrolidin-1-yl-pyrimidine as an off-white solid. EI mass spectrum, m/e: 197 (M calculated for $C_9H_{12}N_3Cl$: 197).

Example 50

In analogy to example 49, from 2-chloro-4-methyl-6-pyrrolidin-1-yl-pyrimidine (183 mg, 0.924 mmol), product of example 49b), and 4-vinylpyridine (192 mg, 1.83 mmol), with $Pd_2(dba)_3$ as catalyst, $P(tBu)_3$ as phosphine ligand and $Cs_2CO_3$ as a base, there was obtained (E)-4-methyl-2-(2-pyridin-4-yl-vinyl)-6-pyrrolidin-1-yl-pyrimidine (118 mg, 47%) as a light-brown solid. ISP mass spectrum, m/e: 267.3 (M+1 calculated for $C_{16}H_{18}N_4$: 267).

Example 51 a) In analogy to example 49, from (2-bomo-6-pyrrolidin-1-yl-pyrimidin-4-yl)-methyl-amine (100 mg, 0.39 mmol)

and 2-vinylpyridine (204 mg, 1.9 mmol) there was obtained methyl-[2-(2-pyridin-2-yl-vinyl)-6-pyrrolidin-1-yl-pyrimidin-4-yl]-amine (63 mg, 57.6%) as an amorphous yellow solid. ISP mass spectrum, m/e: 282.2 (M+1 calculated for $C_{19}H_{19}N_5$: 282).

Preparation of the Starting Material:

b) In analogy to example 49b), from (2,6-dibromo-pyrimidine-4-yl)-methyl-amine (500 mg, 1.9 mmol) and pyrrolidine (266 mg, 3.8 mmol) there was obtained (2-bomo-6-pyrrolidin-1-yl-pyrimidin-4-yl)-methyl-amine (412 mg, 85.6%) as an white solid. ISP mass spectrum, m/e: 257.1 (M+1 calculated for $C_9H_{13}BrN_4$: 257).

c) The above starting material (2,6-dibromo-pyrimidine-4-yl)-methyl-amine was prepared from 2,4,6-tribromopyrimidine (JACS, 78, 2136) on treatment with methylamine in EtOH as a white solid of melting point: 201–202° C.

Example 52 a) In analogy to example 49, from (2-bomo-6-pyrrolidin-1-yl-pyrimidin-4-yl)-methyl-amine (150 mg, 5.8 mmol), product of example 51b), and 4-vinylpyridine (306 mg, 2.9 mmol) there was obtained methyl-[2-(4-pyridin-2-yl-vinyl)-6-pyrrolidin-1-yl-pyrimidin-4-yl]-amine (83 mg, 50.5%) as a yellow solid. ISP mass spectrum, m/e: 282.2 (M+1 calculated for $C_{19}H_{19}N_5$: 282).

Example A

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Upon reading the present specification, various alternative embodiments will become obvious to the skilled artisan. These variations are to be considered within the scope and spirit of the subject invention, which is only to be limited by the claims that follow and their equivalents.

What is claimed is:

1. A compound of the formula:

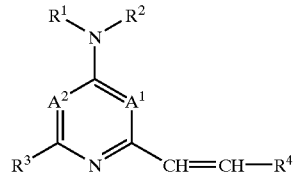

wherein $R^1$ and $R^2$ together with the N atom to which they are attached form a pyrrolidine ring, a pyrrolidine ring that is substituted with alkyl, azetidine ring, or an azetidine ring that is substituted with alkyl;

$R^3$ is alkyl, cycloalkyl, alkoxyalkyl, hydroxyalkyl, haloalkyl, alkoxy, alkoxyalkoxy, hydroxyalkoxyalkyl, hydroxyalkoxy, aralkyl or amino;

$R^4$ is aryl or heteroaryl, wherein $R^4$ is not nitro-furyl or nitro-thienyl;

$A^1$ is CH or N; $A^2$ is CH or N; wherein one of the $A^1$ and $A^2$ is N and the other is CH;

or a pharmaceutically usable salt or ester thereof.

2. The compound according to claim 1, wherein $R^3$ is alkyl or amino.

3. The compound according to claim 1, wherein $R^3$ is methyl or methylamino.

4. The compound according to claim 1, wherein $A^1$ is CH and $A^2$ is N.

5. The compound according to claim 1, wherein $A^1$ is N and $A^2$ is CH.

6. The compound according to claim 1, wherein $R^4$ is phenyl, thienyl, furanyl, pyridinyl, or phenyl that is substituted with one to three substituents independently selected from the group consisting of halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—$CH_2$—O—.

7. A compound of the formula:

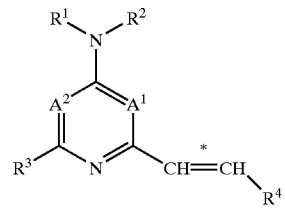

wherein the double bond * is an E double bond and $R^1$ and $R^2$ together with the N atom to which they are attached form a pyrrolidine ring, a pyrrolidine ring that is substituted with alkyl, azetidine ring, or an azetidine ring that is substituted with alkyl;

$R^3$ is alkyl, cycloalkyl, alkoxyalkyl, hydroxyalkyl, haloalkyl, alkoxy, alkoxyalkoxy, hydroxyalkoxyalkyl, hydroxyalkoxy, aralkyl or amino;

$R^4$ is aryl or heteroaryl, wherein $R^4$ is not nitro-furyl or nitro-thienyl;

$A^1$ is CH or N; $A^2$ is CH or N; wherein one of the $A^1$ and $A^2$ is N and the other is CH;

or a pharmaceutically usable salt or ester thereof.

8. The compound according to claim 7, wherein $R^3$ is alkyl or amino.

9. The compound according to claim 7, wherein $R^3$ is methyl or methylamino.

10. The compound according to claim 7, wherein $A^1$ is OH and A2 is N.

11. The compound according to claim 7, wherein $A^1$ is N and $A^2$ is CH.

12. The compound according to claim 7, wherein $R^4$ is phenyl, thienyl, furanyl, pyridinyl, or phenyl that is substituted with one to three substituents independently selected from the group consisting of halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—CH₂—O—.

13. The compound according to claim 9, wherein $R^3$ is methyl.

14. The compound according to claim 13, wherein $R^1$ and $R^2$ together with the N atom to which they are attached form a pyrrolidine ring.

15. The compound according to claim 14, wherein $R^4$ is phenyl that is substituted with one to three substituents independently selected from the group consisting of halogen, hydroxy, alkoxy, amino, cyano, haloalkyl, nitro, 2H-tetrazol-5-yl, alkylthio, alkylsulfonyl, benzyloxy, alkoxycarbonyl, hydroxyalkyl, aminosulfonyl, —O—CH₂—O—.

16. The compound according to claim 15 which is (E)-2-methyl-4-pyrrolidin-1-yl-6-[2-(3-trifluoromethyl-phenyl)-vinyl]-pyrimidine.

17. The compound according to claim 15 which is (E)-4-methyl-6-pyrrolidin-1-yl-2-[2-(3-trifluoromethyl-phenyl)-vinyl]-pyrimidine.

18. The compound according to claim 15 which is (E)-2-methyl-4-[2-(3-nitro-phenyl)-vinyl]-6-pyrrolidin-1-yl-pyrimidine.

19. The compound according to claim 15 which is (E)-2-[2-(3-chloro-phenyl)-vinyl]-4-methyl-6-pyrrolidin-1-yl-pyrimidine.

20. The compound according to claim 15 which is (E)-2-[2-(4-methoxy-phenyl)-vinyl]-4-methyl-6-pyrrolidin-1-yl-pyrimidine.

21. The compound according to claim 15 which is (E)-2-[2-(2,4-dimethoxy-phenyl)-vinyl]-4-methyl-6-pyrrolidin-1-yl-pyrimidine.

22. The compound according to claim 15 which is (E)-4-[2-(4-methyl-6-pyrrolidin-1-yl-pyrimidin-2-yl)-vinyl]-benzonitrile.

23. The compound according to claim 15 which is (E)-2-[2-(3,4-dichloro-phenyl)-vinyl]-4-methyl-6-pyrrolidin-1-yl-pyrimidine.

24. The compound according to claim 15 which is (E)-2-[2-(2,4-dichloro-phenyl)-vinyl]-4-methyl-6-pyrrolidin-1-yl-pyrimidine.

25. The compound according to claim 15 which is (E)-3-[2-(4-methyl-6-pyrrolidin-1-yl-pyrimidin-2-yl)-vinyl]-benzonitrile.

26. The compound according to claim 15 which is (E)-dimethyl-{4-[2-(4-methyl-6-pyrrolidin-1-yl-pyrimidin-2-yl)-vinyl]-phenyl}-amine.

27. The compound according to claim 15 which is (E)-2-(2-benzol[3]dioxol-5-yl-vinyl)-4-methyl-6-pyrrolidin-1-yl-pyrimidine.

28. The compound according to claim 15 which is (E)-2-[2-(3-methoxy-phenyl)-vinyl]-4-methyl-6-pyrrolidin-1-yl-pyrimidine.

29. The compound according to claim 15 which is (E)-2-[2-(3-hydroxy-phenyl)-vinyl]-4-methyl-6-pyrrolidin-1-yl-pyrimidine.

30. The compound according to claim 15 which is (E)-4-methyl-6-pyrrolidin-1-yl-2-{2-[3-(2H-tetrazol-5-yl)-phenyl]-vinyl}-pyrimidine.

31. The compound according to claim 15 which is (E)-4-methyl-2-[2-(4-methylsulfanyl-phenyl)-vinyl]-6-pyrrolidin-1-yl-pyrimidine.

32. The compound according to claim 15 which is (E)-2-[2-(3-fluoro-phenyl)-vinyl]-4-methyl-6-pyrrolidin-1-yl-pyrimidine.

33. The compound according to claim 15 which is (E)-2-[2-(3-benzyloxy-phenyl)-vinyl]-4-methyl-6-pyrrolidin-1-yl-pyrimidine.

34. The compound according to claim 15 which is (E)-3-[2-(4-methyl-6-pyrrolidin-1-yl-pyrimidin-2-yl)-vinyl]-benzoic acid methyl ester.

35. The compound according to claim 15 which is (E)-{3-[2-(4-methyl-6-pyrrolidin-1-yl-pyrimidin-2-yl)-vinyl]-phenyl}-methanol.

36. The compound according to claim 15 which is (E)-2-[2-(3,4-difluoro-phenyl)-vinyl]-4-methyl-6-pyrrolidin-1-yl-pyrimidine.

37. The compound according to claim 15 which is (E)-2-[2-(2,4-difluoro-phenyl)-vinyl]-4-methyl-6-pyrrolidin-1-yl-pyrimidine.

38. The compound according to claim 15 which is (E)-2-[2-(4-fluoro-3-chloro-phenyl)-vinyl]-4-methyl-6-pyrrolidin-1-yl-pyrimidine.

39. The compound according to claim 15 which is (E-) 4-methoxy-N, N-dimethyl-3-[2-(4-methyl-6-pyrrolidin-2-yl-pyrimidin-2-yl)-vinyl]-benzenesulfonamide.

40. The compound according to claim 15 which is (E)-4-methyl-2-[2-(3-nitro-phenyl)-vinyl]-6-piperidin-1-yl-pyrimidine.

41. The compound according to claim 15 which is (E)-3-[2-(4-methyl-6-pyrrolidin-1-yl-pyrimidin-2-yl)-vinyl]-phenylamine.

42. The compound according to claim 15 which is (E)-2-[2-(3,5-dichloro-phenyl)-vinyl]-4-methyl-6-pyrrolidin-1-yl-pyrimidine.

43. The compound according to claim 14, wherein $R^4$ is thienyl.

44. The compound according to claim 43 which is (E)-4-methyl-6-pyrrolidin-1-yl-2-(2-thiophen-2-yl-vinyl)-pyrimidine.

45. The compound according to claim 14, wherein $R^4$ is pyridinyl.

46. The compound according to claim 45 which is (E)-4-methyl-2-(2-pyridin-2-yl-vinyl)-6-pyrrolidin-1-yl-pyrimidine.

47. The compound according to claim 45 which is (E)-4-methyl-2-(2-pyridin-4-yl-vinyl)-6-pyrrolidin-1-yl-pyrimidine.

48. The compound according to claim 13, wherein $R^1$ and $R^2$ together with the N atom to which they are attached form an azetidine ring that is substituted with alkyl.

49. The compound according to claim 48, wherein $R^1$ and $R^2$ together with the N atom to which they are attached form an azetidine ring that is substituted with methyl.

50. The compound according to claim 49 which is (E)-3-{2-[4-(3-methyl-azetidin-1-yl)-6-methyl-pyrimidin-2-yl]-vinyl}-benzonitrile.

51. The compound according to claim 49 which is (E)-2-[2-(3-chloro-phenyl)-vinyl]-4-methyl-6-(3-methyl-azetidin-1-yl)-pyrimidine.

52. The compound according to claim 13 which is (E)-3-{2-[4-(3-hydroxy-pyrrolidin-1-yl)-6-methyl-pyrimidin-2-yl]-vinyl}-benzonitrile.

53. The compound according to claim 13 which is (E)-4-(3-ethoxy-pyrrolidin-1-yl)-2-[2-(3-methoxy-phenyl)-vinyl]-6-methyl-pyrimidine.

54. The compound according to claim 13 which is (E)-3-{2-[4-(3-ethoxy-pyrrolidin-1-yl)-6-methyl-pyrimidin-2-yl]-vinyl}-benzonitrile.

55. The compound according to claim 13 which is (E)-4-(3-ethoxy-pyrrolidin-1 yl)2-[2-(3-fluoro-phenyl)-vinyl]-6-methyl-pyrimidine.

56. The compound according to claim 3 which is 2-[2-(4-methanesulfonyl-phenyl)-vinyl]-4-methyl-6-pyrrolidin-1-yl-pyrimidine.

57. The compound according to claim 9, wherein $R^3$ is methylamino.

58. The compound according to claim 57, wherein $R^1$ and $R^2$ together with the N atom to which they are attached form a pyrrolidine ring.

59. The compound according to claim 58 which is (E)-methyl-[2-(2-pyridin-4-yl-vinyl)-6-pyrrolidin-1-yl-pyrimidin-4-yl]-amine.

60. The compound according to claim 58 which is (E)-methyl-[2-(2-pyridin-2-yl-vinyl)-6-pyrrolidin-1-yl-pyrimidin-4-yl]-amine.

\* \* \* \* \*

UNITED STATES PATENT AND TRADEMARK OFFICE
CERTIFICATE OF CORRECTION

PATENT NO. : 6,657,060 B2
DATED : December 2, 2003
INVENTOR(S) : Volker Breu et al.

It is certified that error appears in the above-identified patent and that said Letters Patent is hereby corrected as shown below:

Title page,
Item [73], Assignee, delete "Hoffman-La Roche Inc., Nutley, NJ (US)"
and insert -- Hoffmann-La Roche Inc., Nutley, NJ (US) --

Column 35,
Line 5, delete "The compound according to claim 7, wherein $A^1$ is OH and A2 is N."
and insert -- The compound according to claim 7, wherein $A^1$ is CH and $A^2$ is N. --
Line 59, delete "The compound according to claim 15 which is (E)-2-(2-benzo[3] dioxol-5-yl-vinyl)-4-methyl-6-pyrrolidin-1-yl-pyrimidine." and insert -- The compound according to claim 15 which is (E)-2-(2-benzo[1,3]dioxol-5-yl-vinyl)-4-methyl-6-pyrrolidin-1-yl-pyrimidine. --

Column 36,
Line 38, delete "The compound according to claim 15 which is (E-)4-methoxy-N,N-dimethyl-3-[2-(4-methyl-6-pyrrolidin-2-yl-pyrimidin-2-yl)-vinyl]-benzenesulfonamide." and insert -- The compound according to claim 15 which is (E-)4-methoxy-N,N-dimethyl-3-[2-(4-methyl-6-pyrrolidin-1-yl-pyrimidin-2-yl)-vinyl]-benzenesulfonamide.--

Column 37,
Line 7, delete "The compound according to claim 13 which is (E)-4-(3-ethoxy-pyrolidin-1-yl)2-[2-(3-fluoro-phenyl)-vinyl]-6-methyl-pyrimidine." and insert -- The compound according to claim 17 which is (E)-4-(3-ethoxy-pyrrolidin-1-yl)-2-[2-(3-fluoro-phenyl)-vinyl]-6-methyl-pyrimidine. --

Signed and Sealed this

Sixth Day of July, 2004

JON W. DUDAS
*Acting Director of the United States Patent and Trademark Office*